United States Patent
Kyle et al.

(10) Patent No.: US 10,149,896 B2
(45) Date of Patent: Dec. 11, 2018

(54) MHC-I RESTRICTED EPITOPES CONTAINING NON-NATURAL AMINO ACID RESIDUES

(71) Applicant: Purdue Pharma L.P., Stamford, CT (US)

(72) Inventors: Donald J. Kyle, Yardley, PA (US); Daniel A. Soltis, Cleveland Heights, OH (US); Lynda G. Tussey, Princeton, NJ (US)

(73) Assignee: Purdue Pharma L.P., Stamford, CT (US)

( * ) Notice: Subject to any disclaimer, the term of this patent is extended or adjusted under 35 U.S.C. 154(b) by 46 days.

(21) Appl. No.: 15/412,329

(22) Filed: Jan. 23, 2017

(65) Prior Publication Data

US 2017/0319670 A1 Nov. 9, 2017

Related U.S. Application Data

(62) Division of application No. 14/820,194, filed on Aug. 6, 2015, now Pat. No. 9,549,972, which is a division of application No. 13/817,261, filed as application No. PCT/IB2011/001809 on Aug. 18, 2011, now Pat. No. 9,109,007.

(60) Provisional application No. 61/374,927, filed on Aug. 18, 2010.

(51) Int. Cl.
| | |
|---|---|
| *A61K 38/08* | (2006.01) |
| *A61K 39/00* | (2006.01) |
| *C07K 14/47* | (2006.01) |
| *C12N 9/02* | (2006.01) |
| *C12N 9/12* | (2006.01) |
| *G01N 33/50* | (2006.01) |
| *G01N 33/68* | (2006.01) |
| *C07K 7/06* | (2006.01) |

(52) U.S. Cl.
CPC ............ *A61K 39/0005* (2013.01); *C07K 7/06* (2013.01); *C07K 14/4747* (2013.01); *C07K 14/4748* (2013.01); *C12N 9/0077* (2013.01); *C12N 9/1241* (2013.01); *G01N 33/505* (2013.01); *G01N 33/6878* (2013.01); *A61K 39/00* (2013.01); *G01N 2333/70539* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 5,440,013 A | 8/1995 | Kahn | |
| 6,338,945 B1 | 1/2002 | Nicolette | |
| 6,579,970 B2 | 6/2003 | Nicolette | |
| 6,716,809 B1 | 4/2004 | Schultz et al. | |
| 9,109,007 B2 * | 8/2015 | Kyle .................. | C07K 14/4747 |
| 9,549,972 B2 | 1/2017 | Kyle et al. | |
| 2006/0057673 A1 | 3/2006 | Liu et al. | |

FOREIGN PATENT DOCUMENTS

| | | |
|---|---|---|
| EP | 2 119 726 A1 | 11/2009 |
| WO | WO 2003/084467 | 10/2003 |
| WO | WO 2006/014579 A2 | 2/2006 |
| WO | WO 2006/138562 A2 | 12/2006 |

OTHER PUBLICATIONS

Guichard, J. Med. Chem. 2000, 43, 3803-3808 (Year: 2000).*
Baratin, M., et al., "Amino Acid Modifications in the Wild Type Sequence p53 232-240 Overcome the Poor Immunogenicity of this Self Tumour Epitope," *J. Peptide Science* 8:327-334, European Peptide Society and John Wiley & Sons, Ltd., United States (2002).
Blanchet, J-S., et al., "A New Generation of Melan-A/MART-1 Peptides That Fulfill Both Increased Immunogenicity and High Resistance to Biodegredation: Implication for Molecular Anti-Melanoma Immunotherapy," *The Journal of Immunology* 167:5852-5861, The American Association of Immunologists, United States (2001).
Guichard, G., et al., "Partially Modified Retro-Inverso Pseudopeptides as Non-natural Ligands for the Class I Histocompatibility Molecule HLA-A2," *J. Med. Chem.* 39:2030-2039, American Chemical Society, United States (1996).
Webb, A.I, et al., "T Cell Determinants Incorporating β-Amino Acid Residues Are Protease Resistant and Remain Immunogenic In Vivo," *The Journal of Immunology* 175:3810-3818, The American Association of Immunologists, United States (2005).
International Search Report for International Application No. PCT/IB2011/001909, European Patent Office, Netherlands, dated Jul. 18, 2012.
International Preliminary Report on Patentability for International Application No. PCT/IB2011/001909, International Bureau of WIPO, Switzerland, dated Feb. 19, 2013.
Bianco, A., et al., "New Synthetic Non-peptide Ligands for Classical Major Histocompatibility Complex Class I Molecules," *The Journal of Biological Chemistry* 273: 28759-28765, The American Society for Biochemisty and Molecular Biology Inc., United States (1998).
Bolin, D., et al., "Peptide and Peptide Mimetic Inhibitors of Antigen Presentation by HLA-DR Class II MHC Molecules, Design, Structure-Activity Relationships, and X-ray Crystal Structures," *J. Med. Chem.* 43: 2135-2148, American Chemical Society, United States (2000).

(Continued)

*Primary Examiner* — Satyanarayana R Gudibande
(74) *Attorney, Agent, or Firm* — Sterne, Kessler, Goldstein & Fox P.L.L.C.

(57) ABSTRACT

The invention provides for the synthesis of more effective generators of a T-cell immune response by providing peptide derivatives that are MHC class I-restricted antigens. The peptide derivatives of the present invention are prepared or derived from a parent peptide of 8 to 11 amino acid residues in length, wherein the peptide derivative contains a non-natural amino acid substituted in place of a naturally-occurring amino acid residue at one or more primary anchor positions in the parent peptide or at position 6, position 7, or the C-terminus.

9 Claims, No Drawings

Specification includes a Sequence Listing.

(56) References Cited

OTHER PUBLICATIONS

Dédier, S., et al., "Structure-Based Design of Nonnatural Ligands for the HLA-B27 Protein," *J. of Receptor & Signal Transduction Research* 19: 645-657, Marcel Dekker, Inc., United States (1999).

Douat-Casassus, C., et al., "Synthetic Anticancer Vaccine Candidates: Rationale Design of Antigenic Peptide Mimetics That Activate Tumor-Specific T-Cells," *J Med. Chem.* 50: 1598-1609, American Chemical Society, United States (2007).

Gómez-Nuñez, M., et al., "Non-Natural and Photo-Reactive Amino Acids as Biochemical Probes of Immune Function," *PloS One* 3: 1-9, Gómez-Nuñez et al., (2008).

Guichard, G., et al., "Efficient Binding of Reduced Peptide Bond Pseudopeptides to Major Histocompatibility Complex Class I Molecule," *The Journal of Biological Chemistry* 270:26057-26059, The American Society for Biochemistry and Molecular Biology, United States (1995).

Guichard, G., et al., "Melanoma Peptide MART-1 (27-35) Analogues with Enhanced Binding Capacity to the Human Class I Histocompatibility Molecule HLA-A2 by Introduction of a β-Amino Acid Residue: Implications for Recognition by Tumor-Infiltrating Lymphocytes," *J. Med. Chem.* 43: 3803-3808, American Chemical Society, United States (2000).

Haro, K., et al., "Photo-Reactive and Non-Natural Amino Acid Epitopes of Human WT1 Enhance Imirnunogenicitv and Allow Kinetic Study of Antigen Processing," *ASH Annual Meeting Abstracts, Part 1*, 118: 684a (Abstract 2311), American Society of Hematology, United States (2007).

Herve, M., et al., "On the Immunogenic Properties of Retro-Inverso Peptides. Total Retro-Inversion of T-Cell Epitopes Causes a Loss of Binding to MHC II Molecules," *Molecular Immunology* 34: 157-163, Elsevier Science Ltd., Netherlands (1997).

Hohsaka, T., et al,, "Incorporation of Non-Natural Amino Acids Into Proteins," *Current Opinion in Chemical Biology* 6: 809-815, Elsevier Science Ltd., Netherlands (2002).

Hruby, V., et al., "Emerging Approaches in the Molecular Design of Receptor-Selective Peptide Ligands: Conformational, Topographical and Dynamic Considerations," *Biochem. J.* 268: 249-262, Portland Press, United Kingdom (1990).

Jones, M., et al., "Synthesis and Ex Vivo Profiling of Chemically Modified Cytomegalovirus CMVpp65 Epitopes," *J. Pept. Sci.* 14: 313-320, European Peptide Society and John Wiley & Sons, Ltd., United States (2008).

Kanodia, S., and Kast, W., "Peptide-Based Vaccines for Cancer: Realizing their Potential," *Expert Rev, Vaccines* 7: 1533-1545, Informa., Switzerland (2008).

Kazmierski, W., et al., "Topographic Design of Peptide Neurotransmitters and Hormones on Stable Backbone Templates: Relation of Conformation and Dynamics to Bioactivity," *J. Am. Chem. Soc.* 113: 2275-2283, American Chemical Society, United States (1991).

Krebs, S., and Rognan, D., "From Peptides to Peptidomimetics: Design of Nonpeptide Ligands for Major Histocompatibility Proteins," *Pharmaceutica Acta Helvetiae* 73: 173-181, Elsevier Science B.V., Netherlands (1998).

Krebs, S., et al., "Binding of Rationally Designed Non-natural Peptides to the Human Leukocyte Antigen HLA-B *2705," *Journal of Peptide Science* 4: 378-388, European Peptide Society and John Wiley & Sons, Ltd., United States (1998).

Krebs, S., et al., "Substituting Nonpeptidic Spacers for the T Cell Receptor-binding Part of Class I Major Histocompatibility Complex-binding Peptides," *The Journal of Biological Chemistry* 278: 19072-19079, The American Society for Biochemistry and Molecular Biology, Inc., United States (1998).

Marschütz, M.K., et al., "improvement of the Enzymatic Stability of a Cytotoxic T-lymphocyte-epitope Model Peptide for its Oral Administration," *Peptides* 23: 1727-1733, Elsevier Science, Inc., Netherlands (2002).

McGregor, D., "Discovering and Improving Novel Peptide Therapeutics," *Curr. Opin. Pharmacol.* 8: 616-619, Elsevier Ltd., Netherlands (2008).

Meng, W., et al., "Rational Design of Nonnatural Peptides for the Human Histocompatibility Antigen HLA-A2," *Pharm. Res.* 13: S-139 (Abstract MNPC 5002), Plenum Publishing Corporation, United States (1996).

Mézière, C., et al., "In Vivo T Helper Cell Response to Retro-Inverso Peptidomimetics[1]," *The Journal of Immunology* 159: 3230-3237, The American Association of Immunologists, United States (1997).

Mocellin, S., et al., "Peptide-Based Anticancer Vaccines: Recent Advances and Future Perspectives," *Current Medicinal Chemistry* 16: 4779-4796, Bentham Science Publishers Ltd., United Arab Emirates (2009).

Poenaru, S., et al., "Nonapeptide Analogues Containing (R)-3-Hydroxybutanoate and β-Homoalariine Oligomers: Synthesis and Binding Affinity to a Class I Major Histocompatibility Complex Protein,", *J. Med. Chem.* 42: 2318-2331, American Chemical Society, United States (1999).

Purcell, A., et al., "More than One Reason to Rethink the Use of Peptides in Vaccine Design," *Nat. Rev. Drug Discov.* 6: 404-414, Nature Publishing Group, United Kingdom (2007).

Raghavan, M., et al., "Extended Repertoire of Permissible Peptide Ligands for HLA-B*2702," *Protein Science* 5: 2080-2088, The Protein Society, United States (1996).

Rognan, D., et al., "Molecular Dynamics Simulation of MHC-Peptide Complexes as a Tool for Predicting Potential T Cell Epitopes," *Biochemistry* 33: 11476-11485, American Chemical Society, United States (1994).

Rognan, D., et al., "Rational Design of Nonnatural Peptides as High-Affinity Ligands for the HLA-B*2705 Human Leukocyte Antigen," *Proc. Natl. Acad. Sci* 92: 753-757, National Academy of Sciences, United States (1995).

Rognan, D., et al., "Fine Specificity of Antigen Binding to Two Class I Major Histocompatibility Proteins (B*2705 and B*2703) Differing in a Single Amino Acid Residue*," *Journal of Computer-Aided Molecular Design* 11: 463-478, Kluwer Academic Publishers, Netherlands (1997).

Rognan, D., et al., "Predicting Binding Affinities of Protein Ligands from Three-Dimensional Models: Application to Peptide Binding to Class I Major Histocompatibility Proteins," *J. Med Chem.* 42:4650-4658. American Chemical Society, United States (1999).

Rovero, P., et al., "Augmentation of the Affinity of HLA Class I-binding Peptides Lacking Primary Anchor Residues by Manipulation of the Secondary Anchor Residues," *Journal of Peptide Science* 1: 266-273, European Peptide Society and John Wiley & Sons, Ltd. (1995).

Scapozza, L., et al., "Molecular Dynamics and Structure-Based Drug Design for Predicting Non-Natural Nonapeptide Binding to a Class I MHC Protein," *Acta Cryst.* D51: 541-549, International Union of Crystallography, Great Britain (1995).

Steer, D., et al., "β-Amino Acids: Versatile Peptidomimetics," *Current Medicinal Chemistry* 9: 811-822, Bentham Science Publishers Ltd., United Arab Emirates (2002).

Weiss, G., et al., "A Tricyclic Ring System Replaces the Variable Regions of Peptides Presented by Three Alleles of Human MHC Class I Molecules," *Chemistry & Biology* 2: 401-407, Current Biology Ltd.(Elsevier Inc.), United States (1995).

Weiss, G., et al., "Covalent HLA-B27/Pepticle Complex Induced by Specific Recognition of an Aziridine Mimic of Arginine," *Proc. Natl. Acad. Sci* 93: 10945-10945, National Academy of Sciences, United States (1996).

\* cited by examiner

SEQUENCE LISTING

<160> NUMBER OF SEQ ID NOS: 49

<210> SEQ ID NO 1
<211> LENGTH: 9
<212> TYPE: PRT
<213> ORGANISM: Artificial
<220> FEATURE:
<223> OTHER INFORMATION: MART-1 nonamer

<400> SEQUENCE: 1

Ala Ala Gly Ile Gly Ile Leu Thr Val
1               5

<210> SEQ ID NO 2
<211> LENGTH: 10
<212> TYPE: PRT
<213> ORGANISM: Artificial
<220> FEATURE:
<223> OTHER INFORMATION: MART-1 decamer

<400> SEQUENCE: 2

Glu Ala Ala Gly Ile Gly Ile Leu Thr Val
1               5                   10

<210> SEQ ID NO 3
<211> LENGTH: 9
<212> TYPE: PRT
<213> ORGANISM: Artificial
<220> FEATURE:
<223> OTHER INFORMATION: MART-1 nonamer peptide derivatives
<220> FEATURE:
<221> NAME/KEY: misc_feature
<222> LOCATION: (2)..(2)
<223> OTHER INFORMATION: Xaa can be any non-naturally occurring amino
      acid

<400> SEQUENCE: 3

Ala Xaa Gly Ile Gly Ile Leu Thr Val
1               5

<210> SEQ ID NO 4
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is beta-cyclopropylalanine

<400> SEQUENCE: 4

Ala Xaa Gly Ile Gly Ile Leu Thr Val
1               5

<210> SEQ ID NO 5
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is aminocyclopentyl carboxylic acid

<400> SEQUENCE: 5

Ala Xaa Gly Ile Gly Ile Leu Thr Val
1               5

```
<210> SEQ ID NO 6
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: MISC_FEATURE
<222> LOCATION: (2)..(2)
<223> OTHER INFORMATION: Xaa is L-cyclohexylglycine

<400> SEQUENCE: 6

Ala Xaa Gly Ile Gly Ile Leu Thr Val
1               5

<210> SEQ ID NO 7
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: MISC_FEATURE
<222> LOCATION: (2)..(2)
<223> OTHER INFORMATION: Xaa is L-cyclopentylglycine

<400> SEQUENCE: 7

Ala Xaa Gly Ile Gly Ile Leu Thr Val
1               5

<210> SEQ ID NO 8
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: MISC_FEATURE
<222> LOCATION: (2)..(2)
<223> OTHER INFORMATION: Xaa is L-6,6-difluoro-bicyclo[3.1.0]
      hexylglycine

<400> SEQUENCE: 8

Ala Xaa Gly Ile Gly Ile Leu Thr Val
1               5

<210> SEQ ID NO 9
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: MISC_FEATURE
<222> LOCATION: (2)..(2)
<223> OTHER INFORMATION: Xaa is L-isopropenealanine

<400> SEQUENCE: 9

Ala Xaa Gly Ile Gly Ile Leu Thr Val
1               5

<210> SEQ ID NO 10
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: MISC_FEATURE
```

```
<222> LOCATION: (2)..(2)
<223> OTHER INFORMATION: Xaa is L-phenylglycine

<400> SEQUENCE: 10

Ala Xaa Gly Ile Gly Ile Leu Thr Val
1               5

<210> SEQ ID NO 11
<211> LENGTH: 9
<212> TYPE: PRT
<213> ORGANISM: Artificial
<220> FEATURE:
<223> OTHER INFORMATION: MART-1-based peptide derivative
<220> FEATURE:
<221> NAME/KEY: MISC_FEATURE
<222> LOCATION: (2)..(2)
<223> OTHER INFORMATION: Xaa is L-styrylalanine

<400> SEQUENCE: 11

Ala Xaa Gly Ile Gly Ile Leu Thr Val
1               5

<210> SEQ ID NO 12
<211> LENGTH: 10
<212> TYPE: PRT
<213> ORGANISM: Artificial
<220> FEATURE:
<223> OTHER INFORMATION: MART-1-decamer peptide derivatives
<220> FEATURE:
<221> NAME/KEY: misc_feature
<222> LOCATION: (2)..(2)
<223> OTHER INFORMATION: Xaa can be any non-naturally occurring amino
      acid

<400> SEQUENCE: 12

Glu Xaa Ala Gly Ile Gly Ile Leu Thr Val
1               5                   10

<210> SEQ ID NO 13
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is beta-cyclopropylalanine

<400> SEQUENCE: 13

Glu Xaa Ala Gly Ile Gly Ile Leu Thr Val
1               5                   10

<210> SEQ ID NO 14
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is aminocyclopentyl carboxylic acid

<400> SEQUENCE: 14

Glu Xaa Ala Gly Ile Gly Ile Leu Thr Val
1               5                   10

<210> SEQ ID NO 15
```

```
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is L-cyclohexylglycine

<400> SEQUENCE: 15

Glu Xaa Ala Gly Ile Gly Ile Leu Thr Val
1               5                   10

<210> SEQ ID NO 16
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is L-cyclopentylglycine

<400> SEQUENCE: 16

Glu Xaa Ala Gly Ile Gly Ile Leu Thr Val
1               5                   10

<210> SEQ ID NO 17
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is L-6,6-difluoro-bicyclo[3.1.0]hexylglycin

<400> SEQUENCE: 17

Glu Xaa Ala Gly Ile Gly Ile Leu Thr Val
1               5                   10

<210> SEQ ID NO 18
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is L-isopropenealanine

<400> SEQUENCE: 18

Glu Xaa Ala Gly Ile Gly Ile Leu Thr Val
1               5                   10

<210> SEQ ID NO 19
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is L-phenylglycine

<400> SEQUENCE: 19
```

```
Glu Xaa Ala Gly Ile Gly Ile Leu Thr Val
1               5                   10

<210> SEQ ID NO 20
<211> LENGTH: 10
<212> TYPE: PRT
<213> ORGANISM: Artificial
<220> FEATURE:
<223> OTHER INFORMATION: MART-1-based peptide derivative
<220> FEATURE:
<221> NAME/KEY: misc_feature
<222> LOCATION: (2)..(2)
<223> OTHER INFORMATION: Xaa is L-styrylalanine

<400> SEQUENCE: 20

Glu Xaa Ala Gly Ile Gly Ile Leu Thr Val
1               5                   10

<210> SEQ ID NO 21
<211> LENGTH: 9
<212> TYPE: PRT
<213> ORGANISM: Artificial
<220> FEATURE:
<223> OTHER INFORMATION: Survivin nonamer

<400> SEQUENCE: 21

Ile Ser Thr Phe Lys Asn Trp Pro Phe
1               5

<210> SEQ ID NO 22
<211> LENGTH: 9
<212> TYPE: PRT
<213> ORGANISM: Artificial
<220> FEATURE:
<223> OTHER INFORMATION: Survivin nonamer peptide derivatives
<220> FEATURE:
<221> NAME/KEY: misc_feature
<222> LOCATION: (2)..(2)
<223> OTHER INFORMATION: Xaa can be any non-naturally occurring amino
      acid

<400> SEQUENCE: 22

Ile Xaa Thr Phe Lys Asn Trp Pro Phe
1               5

<210> SEQ ID NO 23
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is beta-cyclopropylalanine

<400> SEQUENCE: 23

Ile Xaa Thr Phe Lys Asn Trp Pro Phe
1               5

<210> SEQ ID NO 24
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
```

<223> OTHER INFORMATION: Xaa is aminocyclopentyl carboxylic acid

<400> SEQUENCE: 24

Ile Xaa Thr Phe Lys Asn Trp Pro Phe
1               5

<210> SEQ ID NO 25
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-cyclohexylglycine

<400> SEQUENCE: 25

Ile Xaa Thr Phe Lys Asn Trp Pro Phe
1               5

<210> SEQ ID NO 26
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-cyclopentylglycine

<400> SEQUENCE: 26

Ile Xaa Thr Phe Lys Asn Trp Pro Phe
1               5

<210> SEQ ID NO 27
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-6,6-difluoro-bicyclo[3.1.0]
      hexylglycine

<400> SEQUENCE: 27

Ile Xaa Thr Phe Lys Asn Trp Pro Phe
1               5

<210> SEQ ID NO 28
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-isopropenealanine

<400> SEQUENCE: 28

Ile Xaa Thr Phe Lys Asn Trp Pro Phe
1               5

<210> SEQ ID NO 29
<211> LENGTH: 9

```
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-phenylglycine

<400> SEQUENCE: 29

Ile Xaa Thr Phe Lys Asn Trp Pro Phe
1               5

<210> SEQ ID NO 30
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-styrylalanine

<400> SEQUENCE: 30

Ile Xaa Thr Phe Lys Asn Trp Pro Phe
1               5

<210> SEQ ID NO 31
<211> LENGTH: 9
<212> TYPE: PRT
<213> ORGANISM: Artificial
<220> FEATURE:
<223> OTHER INFORMATION: Survivin nonamer sequence

<400> SEQUENCE: 31

Lys Val Arg Arg Ala Ile Glu Gln Leu
1               5

<210> SEQ ID NO 32
<211> LENGTH: 9
<212> TYPE: PRT
<213> ORGANISM: Artificial
<220> FEATURE:
<223> OTHER INFORMATION: Survivin nonamer peptide derivatives
<220> FEATURE:
<221> NAME/KEY: misc_feature
<222> LOCATION: (2)..(2)
<223> OTHER INFORMATION: Xaa can be any non-naturally occurring amino
      acid

<400> SEQUENCE: 32

Lys Xaa Arg Arg Ala Ile Glu Gln Leu
1               5

<210> SEQ ID NO 33
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is beta-cyclopropylalanine

<400> SEQUENCE: 33

Lys Xaa Arg Arg Ala Ile Glu Gln Leu
1               5
```

```
<210> SEQ ID NO 34
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is aminocyclopentyl carboxylic acid

<400> SEQUENCE: 34

Lys Xaa Arg Arg Ala Ile Glu Gln Leu
1               5

<210> SEQ ID NO 35
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-cyclohexylglycine

<400> SEQUENCE: 35

Lys Xaa Arg Arg Ala Ile Glu Gln Leu
1               5

<210> SEQ ID NO 36
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-cyclopentylglycine

<400> SEQUENCE: 36

Lys Xaa Arg Arg Ala Ile Glu Gln Leu
1               5

<210> SEQ ID NO 37
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-6,6-difluoro-bicyclo[3.1.0]
      hexylglycine

<400> SEQUENCE: 37

Lys Xaa Arg Arg Ala Ile Glu Gln Leu
1               5

<210> SEQ ID NO 38
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
```

<223> OTHER INFORMATION: Xaa is L-isopropenealanine

<400> SEQUENCE: 38

Lys Xaa Arg Arg Ala Ile Glu Gln Leu
1               5

<210> SEQ ID NO 39
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-phenylglycine

<400> SEQUENCE: 39

Lys Xaa Arg Arg Ala Ile Glu Gln Leu
1               5

<210> SEQ ID NO 40
<211> LENGTH: 9
<212> TYPE: PRT
<213> ORGANISM: Artificial
<220> FEATURE:
<223> OTHER INFORMATION: Survivin-based peptide derivative
<220> FEATURE:
<221> NAME/KEY: misc_feature
<222> LOCATION: (2)..(2)
<223> OTHER INFORMATION: Xaa is L-styrylalanine

<400> SEQUENCE: 40

Lys Xaa Arg Arg Ala Ile Glu Gln Leu
1               5

<210> SEQ ID NO 41
<211> LENGTH: 9
<212> TYPE: PRT
<213> ORGANISM: Artificial
<220> FEATURE:
<223> OTHER INFORMATION: MART-1 peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (6)..(6)
<223> OTHER INFORMATION: Xaa can be any non-naturally occurring amino
      acid

<400> SEQUENCE: 41

Ala Xaa Gly Ile Gly Xaa Leu Thr Val
1               5

<210> SEQ ID NO 42
<211> LENGTH: 9
<212> TYPE: PRT
<213> ORGANISM: Artificial
<220> FEATURE:
<223> OTHER INFORMATION: MART-1 peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (9)..(9)

```
<223> OTHER INFORMATION: Xaa can be any non-naturally occurring amino
      acid

<400> SEQUENCE: 42

Ala Xaa Gly Ile Gly Ile Leu Thr Xaa
1               5

<210> SEQ ID NO 43
<211> LENGTH: 10
<212> TYPE: PRT
<213> ORGANISM: Artificial
<220> FEATURE:
<223> OTHER INFORMATION: MART-1 peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (7)..(7)
<223> OTHER INFORMATION: Xaa can be any non-naturally occurring amino
      acid

<400> SEQUENCE: 43

Glu Xaa Ala Gly Ile Gly Xaa Leu Thr Val
1               5                   10

<210> SEQ ID NO 44
<211> LENGTH: 10
<212> TYPE: PRT
<213> ORGANISM: Artificial
<220> FEATURE:
<223> OTHER INFORMATION: MART-1 peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (10)..(10)
<223> OTHER INFORMATION: Xaa can be any non-naturally occurring amino
      acid

<400> SEQUENCE: 44

Glu Xaa Ala Gly Ile Gly Ile Leu Thr Xaa
1               5                   10

<210> SEQ ID NO 45
<211> LENGTH: 9
<212> TYPE: PRT
<213> ORGANISM: Artificial
<220> FEATURE:
<223> OTHER INFORMATION: Survivin peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (6)..(6)
<223> OTHER INFORMATION: Xaa can be any non-naturally occurring amino
      acid

<400> SEQUENCE: 45

Ile Xaa Thr Phe Lys Xaa Trp Pro Phe
1               5

<210> SEQ ID NO 46
```

```
<211> LENGTH: 9
<212> TYPE: PRT
<213> ORGANISM: Artificial
<220> FEATURE:
<223> OTHER INFORMATION: Survivin peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (9)..(9)
<223> OTHER INFORMATION: Xaa can be any non-naturally occurring amino
      acid

<400> SEQUENCE: 46

Ile Xaa Thr Phe Lys Asn Trp Pro Xaa
1               5

<210> SEQ ID NO 47
<211> LENGTH: 9
<212> TYPE: PRT
<213> ORGANISM: Artificial
<220> FEATURE:
<223> OTHER INFORMATION: Survivin peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (6)..(6)
<223> OTHER INFORMATION: Xaa can be any non-naturally occurring amino
      acid

<400> SEQUENCE: 47

Lys Xaa Arg Arg Ala Xaa Glu Gln Leu
1               5

<210> SEQ ID NO 48
<211> LENGTH: 9
<212> TYPE: PRT
<213> ORGANISM: Artificial
<220> FEATURE:
<223> OTHER INFORMATION: Survivin peptide derivatives
<220> FEATURE:
<221> NAME/KEY: misc_feature
<222> LOCATION: (2)..(2)
<223> OTHER INFORMATION: Xaa can be any non-naturally occurring amino
      acid
<220> FEATURE:
<221> NAME/KEY: misc_feature
<222> LOCATION: (9)..(9)
<223> OTHER INFORMATION: Xaa can be any non-naturally occurring amino
      acid

<400> SEQUENCE: 48

Lys Xaa Arg Arg Ala Ile Glu Gln Xaa
1               5

<210> SEQ ID NO 49
<211> LENGTH: 10
<212> TYPE: PRT
<213> ORGANISM: Artificial
<220> FEATURE:
<223> OTHER INFORMATION: MART-1 peptide derivative
<220> FEATURE:
<221> NAME/KEY: misc_feature
<222> LOCATION: (2)..(2)
<223> OTHER INFORMATION: Xaa is aminocyclopentyl carboxylic acid
<220> FEATURE:
```

```
<221> NAME/KEY: misc_feature
<222> LOCATION: (7)..(7)
<223> OTHER INFORMATION: Xaa is alpha-methylvaline

<400> SEQUENCE: 49

Glu Xaa Ala Gly Ile Gly Xaa Leu Thr Val
1               5                   10
```

MHC-I RESTRICTED EPITOPES CONTAINING NON-NATURAL AMINO ACID RESIDUES

1. FIELD OF THE INVENTION

The present invention concerns T-cell antigens and methods of generating a T-cell immune response against a tumor antigen or a pathogen. The invention specifically concerns the synthesis of more effective generators of a T-cell immune response ("T-cell immunogens").

2. BACKGROUND OF THE INVENTION

The use of peptides as vaccines for the prevention or treatment of cancer has received considerable attention in recent years as further insight is gained into the steps required to elicit an effective immune response. Even though a greater understanding of these steps has been gained, the success of peptide-based vaccines in the clinic has been very limited. This lack of success in treating cancer is probably due to multiple factors, including the target proteins selected, the nature of the peptides chosen from these proteins and the local environment of the tumor. The selection of proteins as targets for the treatment of cancer is complicated by the fact that many or most tumor antigens that have been identified to date are non-mutated self-antigens, and that the immune response to these self-antigens is restricted by T-cell tolerance. T-cell tolerance can be mediated either centrally or peripherally, and results in the loss of high-avidity cytotoxic T-lymphocytes (CTL) from the immune repertoire that would have the potential to mediate the killing of tumor cells. Consequently, one challenge for the development of effective cancer vaccines is to identify epitopes in tumor antigens to which the immune system has not been tolerized or where tolerance can be overcome.

Unlike antibodies that recognize intact soluble or cell-bound proteins, T-cells recognize fragments of proteins (peptides) that are generated by proteolytic degradation. For CTLs, the peptides generally are comprised of 8 to 11 amino acid residues and are only recognized by cytotoxic T-cells when the peptides are bound to the class I major histocompatibility complex (MHCI). MHCIs are expressed by most cell types and play a critical role in the determination by the immune system of whether a cell is "self" or "non-self" (Whiteside, T. L. and Herberman, R. B., 1995, Curr. Opin. Immunol. 7, 704-711). The steps involved in processing an antigenic protein to generate peptides that can bind to and be presented by MHCIs have been extensively studied. These steps include: (i) internalization of the protein by an antigen-presenting cell (APC); (ii) degradation of the protein into peptides by the APC proteasome; (iii) translocation of the peptides in the endoplasmic reticulum by TAP transporters; and (iv) association of the peptides with the two chains of an MHCI to form a stable MHCI-peptide complex, which is then exported to the cell surface.

Several factors determine which peptides from an antigenic protein are bound to the MHCI and displayed on the cell surface. The ability to be recognized and cleaved by the proteasome, the stability of the peptide in the cytosol, and the efficiency of transport by the TAP transporters are all critical parameters; however, the most important determinant appears to be the ability of the peptide to bind to the MHCI (Chen et al., 1994, J. Exp. Med. 180, 1471-1483). The topology of the class I binding site determines which peptides can bind to the MHCI, and the binding site topology differs among the different class I molecules. Within the set of peptides able to bind to a given class I molecule, there is typically a range of binding affinities such that those with the highest affinity compete the best for display at the cell surface. Peptides preferentially selected by these processes for presentation at the cell surface are referred to as immunodominant epitopes. In general, peptides that bind with high affinity to the MHCI tend to elicit stronger CTL responses than peptides binding with lower affinity (Sette et al., 1994, J. Immunol. 153, 5586-5592). However, it is these higher affinity, immunodominant epitopes derived from self-proteins (such as cancer antigens) to which T-cells have been exposed and tolerized.

Several investigators have developed approaches for identifying CTL epitopes having low MHCI binding affinity, and increasing the binding affinity of these epitopes by making modifications to the native peptide sequence (Parker et al., 1992, J. Immunol. 149, 3580-3587; Tourdot et al., 1997, J. Immunol. 159, 2391-2398; Dionne et al., 2004, Cancer Immunol. Immunother. 53, 307-314). These and other investigators have shown that such modified peptides can be more immunogenic and capable of eliciting enhanced CTL responses in both in vitro and in vivo assays.

In addition to binding affinity, data from other laboratories have shown that the stability of the MHCI-peptide complex is important in determining the immunogenicity of CTL epitopes. Using two CTL epitopes from the Epstein-Barr virus nuclear antigen, it was demonstrated that the epitope forming the more stable MHCI-peptide complex elicited a stronger CTL response when lymphocytes isolated from EBV-seropositive donors were stimulated with a virus-transformed autologous lymphoblastoid cell line (Levitsky et al., 1996, J. Exp. Med. 183, 915-926). From studies examining the binding affinities and dissociation rates of a group of HIV-1 MHCI-binding peptides, it was concluded that the immunogenicity of the HIV-1 derived peptides might be predicted more accurately by the dissociation rate than by the binding affinity of the peptide to MHCI (van der Burg et al., 1996, J. Immunol. 156, 3308-3314). Furthermore, in studies examining multiple modified analogs of a murine p53 epitope, it was observed that modifications enhancing the stability of the MHCI-peptide complex resulted in significantly more potent immunogens (Baratin et al., 2002, J. Peptide Sci. 8, 327-334).

Although modification of CTL epitopes can be effective in increasing the binding affinity of the epitope to the MHCI complex and enhancing the immunogenicity of the epitope, various investigators have shown that these modifications can alter the specificity of the elicited immune response when compared with that of the unmodified "parent" peptide. Substitutions at amino acid "anchor residues" have been shown to alter both the conformation of the MHCI-peptide complex and the conformation of the contacts with the T-cell receptor (Sharma et al., 2001, J. Biol. Chem. 276, 21443-21449; Denkberg et al. 2002, J. Immunol. 169, 4399-4407). Alterations in the sequences of CTL epitopes have also been shown to change the specificity of the immune response elicited in vitro and in patients treated with the modified epitopes (Clay et al., 1999, J. Immunol. 162, 1749-1755; Yang et al., 2002, J. Immunol. 169, 531-539; Dionne et al., 2003, Cancer Immunol. Immunother. 52, 199-206; Okazaki et al., 2003, J. Immunol. 171, 2548-2555). These results indicate that when making modifications to amino acid sequences of low affinity CTL epitopes, it is critical to assess the impact of these changes on the conformation and flexibility of the modified epitope when bound to the MHCI, as well as on the specificity of the immune response elicited by the modified epitope.

Starting about a decade ago, techniques were developed that enabled the analysis of peptides bound to MHCIs (Falk et al., 1991, Nature 351, 290-296; Jardetsky et al., 1991, Nature 353, 326-329). Such techniques have been used extensively to characterize the peptides that bind different MHCI alleles. These studies have led to a general rule that each class I-bound peptide consists of between 8 and 11 amino acid residues. Studies have further shown that those peptides capable of forming a complex with a particular MHCI allele have in common the presence of 2 or 3 largely invariant residues at specific positions in the peptide. X-ray crystallographic studies have provided structural insight into the basis for these conserved residues. These studies have shown that each MHCI folds to form a groove, and it is within this groove that the peptide is displayed. The groove has a specific topology associated with each allele, and is characterized by the presence of several depressions or pockets along its length. Crystallographic studies have shown that the side chains of the conserved peptide residues (the "anchor residues") extend into these pockets, and that the interaction between the MHCI and peptide within these pockets supplies a significant portion of the energy of binding. As such, these largely invariant, allele-specific residues are referred to as "primary anchor residues." Interactions between side chains of amino acids near the termini of the peptide are also important for binding of the peptide to the MHCI, and they are observed in the crystallographic studies to bury into the ends of the MHCI binding groove. Much of the range in binding affinities among peptides that bind to a given MHCI allele is due to sequence variations in this array of primary anchor residues. However, it is also clear that other residues outside the primary anchor positions can contribute to MHCI binding (Kondo et al., 1995, J. Immunol. 155, 4307-4312; Schonbach et al., 1995, J. Immunol. 154, 5951-5958), and these other residues are referred to as "secondary anchor residues". Secondary anchor residues may also contribute to the range in binding affinities among peptides binding to a particular MHCI.

A number of investigators have successfully enhanced the immunogenicity of both viral and tumor peptide epitopes by increasing the affinity of the peptide for the MHCI. Typically, this has been achieved by replacing sub-optimal residues found at the primary anchor positions with an optimal natural residue. In mice, an anchor-modified epitope from mutant Ras binds more effectively to the H-2$K^d$ allele, induces enhanced cytolytic activity in vitro, and elicits a greater T-cell response in vivo than the unmodified parent mutant Ras peptide (Bristol et al., 1998, J. Immunol. 160, 2433-2441). Similar results were also observed in mice transgenic for human HLA-A2. In these experiments, an anchor-modified epitope from HIV reverse transcriptase was shown to be more effective at inducing CTL reactive with the reverse transcriptase than the parent peptide, and afforded greater protection in vivo against a challenge with Vaccinia virus expressing the HIV-1 reverse transcriptase (Okazaki et al., 2003, J. Immunol. 171, 2548-2555). In addition, anchor-modified epitopes from the melanoma antigen gp100 were shown to bind with higher affinity to HLA-A*0201 than did the parent epitopes, and induced melanoma-reactive CTL in peripheral blood leukocytes (PBL) isolated from 7 of 7 HLA-$A2^+$ melanoma patients. In contrast, the unmodified parent epitopes induced melanoma-reactive CTL in PBL from only 2 of the 7 patients (Parkhurst et al., 1996, J. Immunol. 157, 2539-2548).

Alternative approaches to enhancing the binding affinity of CTL epitopes to MHCI include amino acid substitutions at positions other than the primary anchor residues. Systematic analyses of the role of secondary anchor residues in the binding of CTL epitopes to the MHCI have been performed, revealing that amino acid residues at positions other than the primary anchor residues can strongly influence the binding of the epitope (Deres et al., 1993, Cell. Immunol. 151, 158-167; Kondo et al., 1995, J. Immunol. 155, 4307-4312). In addition, studies examining the immunogenicity of two epitopes from ovalbumin indicate that amino acid residues at sites other than the primary anchor sites can significantly influence binding and presentation of an epitope (Chen et al., 1994, J. Exp. Med. 180, 1471-1483). A more general strategy has also been proposed to enhance the binding and immunogenicity of epitopes that bind with low affinity to HLA-A2.1. Studies with multiple low-affinity HLA-A2.1 epitopes show that the introduction of tyrosine at the first position can enhance the binding affinity and immunogenicity of the modified epitope (Pogue et al., 1995, Proc. Natl. Acad. Sci. USA 92, 8166-8170; Toudot et al., 2000, Eur. J. Immunol. 30, 3411-3421; Patent Application Publication US 2004/0072240 A1 by Kosmatopoulos et al.).

Non-natural amino acids have also been used with some success to replace natural amino acids and increase the immunogenicity of CTL epitopes. Using an antigenic peptide from the influenza virus matrix protein, a retro-inverso amide bond substitution was shown to enhance binding of the modified peptide to HLA-A2; however, this retro-inverso modification was only effective when inserted between Position 1 (P1) and Position 2 (P2) (as numbered from the amino terminus of the peptide), and resulted in a significant reduction in binding when used between P2 and P3, or P3 and P4, or P5 and P6, or P8 and P9 (Guichard et al., 1996, J. Med. Chem. 39, 2030-2039).

An alternative approach utilized an epitope from Melan-A (GenBank No. U06654). Melan-A is unrelated to any known gene and is encoded by an approximately 18-kilobase gene comprised of 5 exons (Coulie et al., 1994, J. Exp. Med. 180, 35-42). Similar to other melanoma-associated antigens, Melan-A is expressed in most melanoma tumor samples and normal melanocytes. HLA-A2 restricted melanoma-specific CTLs from nine of ten patients recognize primarily the MART-1 epitope, i.e., amino acid residues 27-35 (AAGIGILTV; SEQ ID NO:1) of Melan-A. Kawakami, Y., et al., J. Exp. Med. 180, 347-352 (1994). The MART-1 epitope of Melan-A has been studied extensively and has been used as a model system for investigating cellular immune responses in humans. Valmori et al., J. Immunol. 160, 1750-1758 (1998). The alternative approach involved the substitution of a β-amino acid at Position 4 (P4), resulting in enhanced binding of the peptide to HLA-A2 and increased stability of the peptide-MHCI complex. However, only one out of three MART-1 specific CTL clones isolated from HLA-A2 restricted human tumor infiltrating lymphocytes (TIL) recognized and lysed target cells pulsed with the modified peptide. Guichard et al., J. Med. Chem. 43:3803-3808 (2000).

In an attempt to reduce biodegradation and enhance the immunogenicity of CTL epitopes, 36 peptide derivatives of the MART-1 epitope were designed based on knowledge of the degradation pathway in human serum. Non-natural amino acids were substituted at positions 1, 2, 8, 9 and 10 of the 10 amino acid MART-1 epitope individually and in combination and these modified MART-1 epitopes were then tested for their resistance to proteolysis and antigenic properties (Blanchet et al., 2001, J. Immunol. 167, 5852-

5861). Eight of the modified epitopes were found to have enhanced stability against degradation when incubated in human serum, and three of these analogs were shown to be more potent than the parental epitope in stimulating in vitro MART-1 specific CTL responses in PBMC from normal donors. Non-natural amino acids have also been used in studies aimed at enhancing the immunogenicity of a poorly immunogenic epitope from murine p53. By replacing cysteine with aminobutyric acid at positions 4 and 8 and methionine with norleucine at positions 3 and 9 in the epitope, the modified peptides bound with higher affinity to MHCI and appeared to be more potent immunogens. Baratin et al., J. Peptide Sci. 8:327-334 (2002).

With a strong scientific rationale, highly promising preclinical results and the frequently observed induction of target-specific immune responses in treated patients, the interest in and efforts directed at the development of effective cancer vaccines continues to increase. A recent study described 645 clinical trials related to cancer vaccines and reported that new cancer vaccine trials had shown a steady increase since 2001 reaching more than 60 new trials each year (Cao, X., et al., 2008, Immunome Research 4, 1-11). However, the results from these clinical trials have been much less encouraging with only rare occurrences of objective tumor regression despite the detection in some patients of robust target-specific immune responses (Mocellin, S., et al., 2009, Curr. Med. Chem. 16, 4779-4796). Investigators have identified a number of factors that likely contribute to the poor clinical results including the selection of suboptimal targets, the presence of mutations in tumor cells that can promote tumor escape and immunosuppressive factors including cells, proteins and chemicals present in the tumor environment. It has been proposed that a successful cancer vaccine will need to address these and other factors by incorporating at least one and most likely multiple optimized epitopes, enhanced delivery systems, adjuvants and co-factors to activate cytotoxic and helper T-cells as well as antigen presenting cells, and strategies to inhibit the immunosuppressive network (Kanodia, S. and Kast, W. M., 2008, Expert Rev. Vaccines 7, 1533-1545).

There is a continuing need in the art for improved methods of generating a T-cell immune response.

3. SUMMARY OF THE INVENTION

The present invention provides a peptide derivative that is an MHC class I ("MHCI") restricted antigen, and which is prepared or derived from a parent peptide of 8 to 11 amino acid residues in length, and preferably either 9 or 10 amino acid residues in length, wherein the peptide derivative contains a non-natural amino acid substituted in place of a naturally occurring amino acid residue at one or more primary anchor positions, for example at one primary anchor position, or at two primary anchor positions. Thus, the invention provides a peptide derivative of a MHCI restricted parent antigen (e.g., parent peptide or parent epitope) comprising a non-natural amino acid at at least one anchor position.

The invention further provides a peptide derivative of a MHCI restricted parent antigen comprising a non-natural amino acid at one anchor position and a second substitution at a second position. The second substitution at a second position may be at a second anchor position, or may be at the C-terminus (PΩ), e.g., for MHCI peptides that do not have an anchor position at the C-terminus, or may be at position 6 (P6) or position 7 (P7).

Any of the peptide derivatives provided by the present invention may or may not be in the form of a pharmaceutically acceptable salt.

The parent peptide is an MHCI restricted antigen and the peptide derivative provided by the present invention is a MHCI restricted antigen that binds at least the same MHCI molecule as the parent peptide, e.g., if the parent peptide binds HLA-A*0201, then the peptide derivative also binds HLA-A*0201. In addition, the peptide derivative of the present invention is able to trigger an expansion of T-cells that are able to bind the parent peptide when it is complexed with MHCI.

The peptide derivatives of the present invention may also have increased immunogenicity in comparison to the parent peptide. In preferred embodiments, the peptide derivative exhibits at least one, or at least two, or at least three, or at least four, or all five of the following properties.

A first property is that the peptide derivative of the present invention generates a T-cell immune response that is greater than the T-cell immune response generated by the parent peptide. In one embodiment, the parent peptide generates a detectable T-cell immune response, but the peptide derivative generates a T-cell immune response which is greater than the T-cell immune response generated by the parent peptide. In another embodiment, the parent peptide does not generate a detectable T-cell immune response, whereas the peptide derivative of the present invention generates a T-cell immune response that can be detected. In additional embodiments, the immune response may be T-cell lysis of target cells, cytokine release, and/or T-cell degranulation.

A second property is that the peptide derivative of the present invention binds to MHCI with an affinity that is higher than the affinity with which the parent peptide binds to MHCI, i.e., the peptide derivative has a lower $K_D$ than the parent peptide.

A third property is that the affinity of T-cell receptors for the complex formed between MHCI and a peptide derivative of the present invention is higher than the affinity of T-cell receptors for the complex formed between MHCI and the parent peptide. This increased affinity may be determined using a tetramer assay (Laugel, B., et al., 2007, J. Biol. Chem. 282, 23799-23810; Holmberg, K., et al., 2003, J. Immunol. 171, 2427-2434; Yee, C., et al., 1999, J. Immunol. 162, 2227-2234).

A fourth property is that a complex formed between MHCI and a peptide derivative of the present invention is more stable (i.e., has a slower off-rate) than a complex formed between MHCI and the parent peptide.

A fifth property is that the peptide derivative of the present invention triggers an expansion of a broader number of T-cell clones that recognize the parent peptide than are triggered by the parent peptide.

In a preferred embodiment, the parent peptide is from 8 to 11 amino acid residues in length, and preferably either 9 or 10 amino acid residues in length.

In one embodiment, the parent peptide is a nonamer (i.e., consisting of 9 amino acid residues).

In another embodiment, the parent peptide is a decamer (i.e., consisting of 10 amino acid residues).

In another embodiment, the substituted amino acid residue is at the P2 anchor position in the parent peptide.

In another embodiment, the parent peptide is a nonamer wherein the substituted amino acid residue is at the P2 anchor position, or a decamer wherein the substituted amino acid residue is at the P2 anchor position.

In one embodiment, the peptide derivative of the present invention is substantially purified, i.e., comprised in a preparation in which the peptide derivative is at least about 70% by weight of the total preparation.

A peptide derivative of the present invention can be further modified so as to enhance one or more beneficial properties thereof, including any one or more of the aforementioned five properties listed above, or another property such as solubility or in vivo half-life, among others. In one non-limiting example, a peptide derivative of the present invention is conjugated to a polyethylene glycol (PEG) molecule of appropriate molecular weight so as to increase the in vivo half-life of the peptide derivative.

The present invention further provides a pharmaceutical composition comprising any of the aforementioned peptide derivatives combined with a pharmaceutically acceptable carrier. The pharmaceutical composition may be adapted for administration by any appropriate route, including by parenteral administration.

The present invention further provides a method of preparing a pharmaceutical composition comprising admixing any of the aforementioned peptide derivatives with a pharmaceutically acceptable carrier.

The present invention further provides a complex comprising an MHCI having a peptide derivative of the present invention bound within its antigen-binding groove.

The present invention further provides a cell comprising an immunogenic cell-surface bound complex consisting of MHCI having a peptide derivative of the present invention bound within its antigen-binding groove. The cell can be any cell expressing MHCI, either naturally or as the result of genetic engineering.

The present invention further provides a method for identifying a peptide derivative that has improved ability to activate and expand a clone of a T-cell, which method comprises:
  (a) preparing a peptide derivative of a parent peptide, wherein the parent peptide is 8 to 11 amino acid residues in length, and preferably 9 or 10 amino acid residues in length, such that the peptide derivative has a non-natural amino acid substituting for an amino acid residue at one or more primary anchor positions in the parent peptide; and
  (b) determining whether the peptide derivative of step (a) is more effective than the parent peptide at activating and expanding one or more T-cell clones.

In one embodiment, the parent peptide can detectably activate and expand the clone of the T-cell, but not as effectively as the peptide derivative.

In another embodiment, the parent peptide cannot detectably activate and expand the clone of the T-cell, whereas the peptide derivative can detectably activate and expand the clone of the T-cell.

The present invention further provides a method for identifying a peptide derivative that has an affinity to MHCI that is higher than the affinity of its parent peptide to MHCI, which method comprises:
  (a) preparing a peptide derivative of a parent peptide, wherein the parent peptide is 8 to 11 amino acid residues in length, and preferably 9 or 10 amino acid residues in length, such that the peptide derivative has a non-natural amino acid substituting for an amino acid residue at one or more primary anchor positions in the parent peptide; and
  (b) determining whether the peptide derivative of step (a) has an affinity for MHCI that is higher than the affinity of the parent peptide for MHCI.

The present invention further provides a method for identifying a peptide derivative, wherein there is a higher affinity of T-cell receptors for the complex formed between MHCI and the peptide derivative than for the complex formed between MHCI and the parent peptide of the peptide derivative, which method comprises:
  (a) preparing a peptide derivative of a parent peptide, wherein the parent peptide is 8 to 11 amino acid residues in length, and preferably 9 or 10 amino acid residues in length, such that the peptide derivative has a non-natural amino acid substituting for an amino acid residue at one or more primary anchor positions in the parent peptide; and
  (b) determining whether there is a higher affinity of T-cell receptors for the complex formed between MHCI and the peptide derivative than for the complex formed between MHCI and the parent peptide.

The present invention further provides a method for identifying a peptide derivative that forms a complex with MHCI that is more stable than the complex formed between the parent peptide and MHCI, which method comprises:
  (a) preparing a peptide derivative of a parent peptide, wherein the parent peptide is 8 to 11 amino acid residues in length, and preferably 9 or 10 amino acid residues in length, such that the peptide derivative has a non-natural amino acid substituting for an amino acid residue at one or more primary anchor positions in the parent peptide; and
  (b) determining whether the peptide derivative of step (a) forms a complex with MHCI that is more stable than the complex formed between the parent peptide and MHCI.

The present invention further provides a method for identifying a peptide derivative that can trigger an expansion of T-cells able to recognize the parent peptide of the peptide derivative, which method comprises:
  (a) preparing a peptide derivative of a parent peptide, wherein the parent peptide is 8 to 11 amino acid residues in length, and preferably 9 or 10 amino acid residues in length, such that the peptide derivative has a non-natural amino acid substituting for an amino acid residue at one or more primary anchor positions in the parent peptide; and
  (b) determining whether the peptide derivative of step (a) can trigger an expansion of T-cells that are able to recognize the parent peptide of the peptide derivative.

The present invention further provides a method for identifying a peptide derivative that can trigger an expansion of a broader number of T-cell clones that recognize the parent peptide than can be triggered by the parent peptide, which method comprises:
  (a) preparing a peptide derivative of a parent peptide, wherein the parent peptide is 8 to 11 amino acid residues in length, and preferably 9 or 10 amino acid residues in length, such that the peptide derivative has a non-natural amino acid substituting for an amino acid residue at one or more primary anchor positions in the parent peptide; and
  (b) determining whether the peptide derivative of step (a) can trigger an expansion of a broader number of T-cell clones that recognize the parent peptide than can be triggered by the parent peptide.

A peptide identified by any of the aforementioned identification methods will exhibit at least one, and preferably at least two, or at least three, or at least four, or all five of the improved properties recited in the aforementioned identification methods.

In one embodiment of any of the aforementioned identification methods, the parent peptide is a nonamer.

In another embodiment of any of the aforementioned identification methods, the parent peptide is a decamer.

In another embodiment of any of the aforementioned identification methods, the substituted amino acid residue is at the P2 anchor position.

In another embodiment of any of the aforementioned identification methods, the parent peptide is a nonamer wherein the substituted amino acid residue is at the P2 anchor position, or a decamer wherein the substituted amino acid residue is at the P2 anchor position.

The present invention further provides a method of using a peptide derivative of the present invention to activate and expand a T-cell clone that is reactive towards a parent peptide. The activated and expanded T-cells can be used to recognize the parent peptide in a subject. This method of use can be practiced by administering the peptide derivative directly to the subject. Alternatively, dendritic-type antigen presenting cells ("dAPCs" or "DCs") can be cultured ex vivo and pulsed with the peptide derivative, and the pulsed dAPCs administered directly to the subject to activate and expand T-cells in vivo. Alternatively, a subject's T-cells can be cultured ex vivo, such that activated expanded T-cells can be administered directly back to the subject. Such methods can be used to obtain a therapeutic benefit in the subject so as to, e.g., treat or prevent a condition such as a cancer or infection. The activated and expanded T-cells can also be used to recognize the parent peptide in a biological sample ex vivo.

The present invention further provides a method of inducing an immune response against a peptide derivative of the present invention. The present invention also provides a method of inducing an immune response against a parent peptide using a peptide derivative of the present invention. The peptide derivative may be administered to a subject to induce an immune response, or may be contacted with immune cells from a subject ex vivo. The peptide derivative may be part of a pharmaceutical or diagnostic composition.

The present invention further provides a method for treating or preventing a condition in a subject, comprising administering a therapeutically effective amount of a peptide derivative of the present invention to a subject in need of such treatment. In one embodiment, said method is for treating said condition in a subject. In one embodiment, the peptide derivative administered to the subject is present in a pharmaceutical composition provided by the present invention. The present invention also provides the peptide derivative of the present invention for use as a medicament.

The condition treated or prevented by a method or medicament of the present invention may be selected from the group consisting of cancers and infections as described further herein. In one embodiment, the cancer is treated by a method of the present invention. In another embodiment, the cancer is prevented by a method of the present invention. In one embodiment, the infection is treated by a method of the present invention. In another embodiment, the infection is prevented by a method of the present invention.

The present invention further provides a use of any of the peptide derivatives of the present invention in the manufacture of a medicament to treat a condition, such as a cancer or an infection, in a subject.

The present invention further provides the peptide derivative of the present invention for use as a medicament, and specifically for use in the treatment or prevention of a cancer or of an infection, and in particular for use in the treatment of a cancer or of an infection.

4. DETAILED DESCRIPTION OF THE INVENTION

The present invention provides a peptide derivative that is an MHCI restricted antigen, and is derived from a parent peptide 8 to 11 amino acid residues in length, preferably 9 or 10 amino acid residues in length, wherein the peptide derivative contains a non-natural amino acid substituted in place of a naturally occurring amino acid residue at one or more primary anchor positions, preferably at two primary anchor positions, and more preferably at one primary anchor position. Thus, the invention provides a peptide derivative of a MHCI restricted parent antigen (e.g., parent peptide or parent epitope), the derivative comprising a non-natural amino acid in at least one primary anchor position. In some embodiments, the anchor position is Position 2 (P2). In some embodiments, the anchor position is at the C-terminus (PΩ). In some embodiments, there is a non-natural amino acid both in position P2 and in position PΩ. See below for additional anchor positions which can be taken by a non-natural amino acid in some embodiments.

The invention further provides a peptide derivative of a MHCI restricted parent antigen comprising a non-natural amino acid at one anchor position, e.g. at position P2, and a second substitution at a second position. In some embodiments, the second position is position 6 (P6) or position 7 (P7). In some embodiments, the second position is the C-terminus (PΩ), e.g., for MHCI peptides that do not have an anchor position at the C-terminus.

The peptide derivative provided by the present invention is a MHCI restricted antigen that binds at least the same MHC molecule as the parent peptide, e.g., if the parent peptide binds HLA-A*0201, then the peptide derivative also binds HLA-A*0201. In addition, the peptide derivative of the present invention is able to trigger an expansion of T-cells that are able to bind the parent peptide when it is complexed with MHCI. A peptide derivative of the invention may also have improved immunogenicity over its parent peptide. The peptide derivatives of the invention do not include the peptides disclosed in the following publications, each of which is incorporated herein by reference in its entirety: Bianco, J. Biol. Chem. 273:28759-65 (1998); Bolin, J. Med. Chem. 43:2135-48 (2000); Dedier, J. Receptor & Signal Transduct. Res. 19 (1-4):645-57 (1999); Douat-Casassus, J. Med. Chem. 50:1598-1609 (2007); Gomez-Nunez, PLoS ONE 3(12):e3938 (2008); Haro, Kurtis J., "Photo-Reactive and Non-Natural Amino Acid Epitopes of Human WT1 Enhance Immunogenicity and Allow Kinetic Study of Antigen Processing," ASH Annual Meeting Abstracts, Part 1, Vol. 118(11):684a, abst. 2311 (2007); Jones, J. Pept. Sci. 14:313-20 (2008); Liu, US 2006/0057673 A1 (2006); Poenaru, J. Med. Chem. 42:2318-31 (1999); Rovero, J. Pept. Sci. 1:266-73 (1995); Schultz, U.S. Pat. No. 6,716,809 B1 (2004); Baratin, J. Pept. Sci. 8:327-34 (2002); Blanchet et al., J. Immunol. 167:5852-61 (2001); Guichard et al., J. Biol. Chem. 270:26057-59 (1995); Guichard et al., J. Med. Chem. 39:2030-39 (1996); Guichard et al., J. Med. Chem. 43:3803-8 (2000); Herve et al., Mol. Immunol. 34:157-63 (1997); Kanodia and Kast, Expert Rev. Vaccines 7:1533-45 (2008); Krebs and Rognan, Pharmaceut. Acta Helv. 73:173-81 (1998); Krebs et al., J. Peptide Sci. 4:378-88 (1998); Krebs et al., J. Biol. Chem. 273:19072-9 (1998); Marschutz et al., Peptides 23:1727-33 (2002); MacGregor, Curr. Opin. Pharmacol. 8:616-19 (2008); Meziere et al., J. Immunol. 159:3230-37 (1997); Mocellin, et al., Curr. Med. Chemistry 16:4779-96 (2009); Peonaru et al., J. Med. Chem. 42:2318-31 (1999); Purcell et al., Nat.

Rev. Drug Discov. 6:404-14 (2007); Rhagavan et al., Protein Sci. 5:2080-88 (1996); Rognan et al., Biochemistry 33:11476-85 (1994); Rognan et al, PNAS 92:753-57 (1995); Rognan et al., J. Computer-Aided Mol. Design 11:463-78 (1997); Rognan, "Molecular modelling of protein-peptide complexes—Application to major histocompatibility proteins," Habilitationsschrift, Eidgenossiche Technische Hochsschule (ETH) Zurich (1998); Rognan et al., J. Med. Chem. 42:4650-58 (1999); Rovero et al., PNAS 92:753-57 (1995); Scapozza et al., Acta Crystallogr. D Biol. Crystallogr. 51(Pt 4):541-9 (1995); Steer et al., Curr. Med. Chem. 9:811-22 (2002); von Grafenstein, Pharm. Res. 13(9) (Suppl):S-139, abstr. MNPC 5002 (1996); Webb et al., J. Immunology 175:3810-18 (2005); Weiss et al., Chem. and Biol. 2:401-7 (1995); Weiss et al., PNAS 93:10945-48 (1996); WO 03/084467 (Euro-Celtique); Rhuby et al., Biochem. J. 268:249-62 (1990); Kazmierski et al., J. Am. Chem. Soc. 113:2275-83 (1991); Hohsaka et al., Curr. Opinion Chem Biol 6:809-15 (2002); Kahn, U.S. Pat. No. 5,440,013; Nicolette, U.S. Pat. No. 6,338,945 and U.S. Pat. No. 6,579,970; and WO 2006/138562 (Mannkind Corporation).

4.1. Definitions

As used herein, the term "naturally occurring amino acid residue" or "natural amino acid" refers to one of the L-amino acids occurring naturally in proteins. As used herein, the term "natural amino acid side chain" refers to a side chain attached to the Cα of one of the natural amino acids. Unless otherwise indicated, the "naturally-occurring amino acid residues" in the peptide sequences disclosed herein are presented using the standard single letter amino acid abbreviations for the twenty naturally occurring amino acids, as follows:

TABLE 1

| Amino Acid | Abbreviation |
| --- | --- |
| Alanine | A |
| Arginine | R |
| Asparagine | N |
| Aspartic Acid | D |
| Cysteine | C |
| Glutamic Acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

As used herein, the term "non-natural amino acid" refers to amino acids that do not naturally occur in proteins, and that contain, by analogy to naturally occurring amino acids, a primary amine, a free carboxylate group and a side chain and that can be inserted into a peptide sequence using conventional peptide synthesis methods. In some embodiments, a non-natural amino acid is conformationally constrained. In some embodiments, a non-natural amino acid has a side chain that is the same as or chemically similar to the side chain of the residue that it replaces.

In some embodiments, a "non-natural amino acid" contains a non-natural side chain. In some embodiments, a non-natural side chain is conformationally constrained. In some embodiments, a non-natural side chain is similar to the natural side chain of the residue that it replaces.

A used herein, the terms "conformationally constrained," "conformation constraining," "conformational constraint," and the like, as used herein, when referring to a non-natural amino acid, generally refer to a non-natural amino acid used to replace (i.e., substitute for) an amino acid residue in a parent peptide such that the peptide resulting from such substitution has less flexibility (i.e., is more conformationally constrained than the parent peptide), as evidenced by increased constraint in the rotation about one or more polymer bond, e.g., by disubstitutions of $C^{\alpha}$ or a substitution at the amide nitrogen, or by fewer rotational degrees of freedom of all available peptide bonds in the backbone, of the peptide derivative. For example, a non-natural amino acid residue provides a conformational constraint relative to the original residue at that position when the rotations about backbone dihedral angles $(\varphi,\psi)$ are constrained by substitutions at $C^{\alpha}$, e.g., αMe-leucine, or at the amide nitrogen.

In some embodiments, the "conformationally constrained" non-natural amino acid is one that, upon substitution into an anchor position, e.g., the P2 position, of the parent peptide, results in the adoption of Phi/Psi backbone angles of −60±30 degrees, and +110±50 degrees, respectively. The adoption of these backbone angles can be determined by standard techniques, including by NMR, X-ray crystallography, or computational structural prediction.

The number of rotational degrees of freedom of all available bonds in the backbone is determined by the number of non-cyclic single bonds connecting multivalent atoms having at least two distinct substituents or having aromatic bonds. For example, a proline residue has one degree of freedom; glycine and alanine have two; serine and valine have three; phenylalanine, leucine and aspartic acid have four; methionine and glutamine have five; and lysine and arginine have six.

The following non-natural amino acids have side chains that are similar to leucine (e.g., the most preferred naturally-occurring amino acid as a P2 anchor in HLA-A0201) and would be suitable for replacing leucine in a parent peptide (e.g., for substitution of a P2 leucine in a HLA-A0201 restricted peptide epitope). They are grouped by the number of degrees of freedom of all available bonds in the backbone: two degrees, aminocyclopropylcarboxylic acid ("ACC"), aminocyclobutylcarboxylic acid ("ACBC"), aminocyclopentylcarboxylic acid ("ACPC"), and aminocyclohexylcarboxylic acid ("ACHC"); three degrees, L-cyclohexylglycine, L-cyclopentylglycine, and L-phenylglycine; four degrees, β-cyclopropylalanine, β-amino-L-n-butyric acid (homoalanine), L-4,5-dehydroleucine, and L-norvaline; and five degrees, L-styrylalanine, and L-norleucine.

Of the foregoing, the amino acids with three or fewer degrees of freedom are conformationally constrained compared, e.g., to leucine and methionine, while those with four degrees of freedom are conformationally constrained compared only to methionine.

As a further example, the replacement of glutamic acid by 1,3-dicarboxyl, 1-amino-cyclobutane would be an example of a substitution of a conformationally constrained residue having an analogous side chain.

As used herein, a "conformationally constrained side chain" is any side chain with fewer degrees of freedom than the side chain of the residue that it replaces.

As used herein, the term "conformationally constrained peptide" means a peptide that results from the replacement of an amino acid in a parent peptide with a more conformationally constrained non-natural amino acid.

In one embodiment, the non-natural amino acid is a Cα disubstituted amino acid. The Cα and the substituents may or may not form a ring. In another embodiment, the non-natural amino acid is an N-substituted amino acid. The non-natural amino acid may be selected from the group consisting of chg, cpg, ACC, ACBC, ACPC, ACHC, phg, β-cp-Ala, styr-Ala, Nle, Abu, γ,δ-Δ-Leu, Nrv, c3a, c5g, dfb and dhl. In one embodiment, this is under the proviso that the peptide is not ENrvAGIGILTV or ELAGIGILTNrv. In another embodiment, the peptide is not a peptide selected from the group consisting of ENrvAGIGILTV, ELAGIGILTNrv, ENrvAGIGILTNrv, ENrvAGIGILTNle, ENleAGIGILTV, ENleAGIGILTNrv, ENleAGIGILTNle, ELAGIGILTNle, EAAGIGILTNrv, and EAAGIGILTNle. In another embodiment, the non-natural amino acid may be selected from the group consisting of chg, cpg, ACC, ACBC, ACPC, ACHC, phg, β-cp-Ala, styr-Ala, Abu, γ,δ-Δ-Leu, c3a, c5g, dfb and dhl.

In another embodiment, the non-natural amino acid is selected from the group consisting of chg (L-cyclohexylglycine), cpg (L-cyclopentylglycine), ACC, ACBC, ACPC, ACHC, phg (L-phenylglycine), β-cyclo-propylalanine (β-cp-Ala), styrylalanine (styr-Ala), norleucine (Nle), β-amino-L-n-butyric acid (Abu), γ,δ-dehydroleucine (γ,δ-Δ-Leu), and norvaline (Nrv). In one embodiment, this is under the proviso that the peptide is not ENrvAGIGILTV or ELAGIGILTNrv. In another embodiment, the peptide is not a peptide selected from the group consisting of ENrvAGIGILTV, ELAGIGILTNrv, ENrvAGIGILTNrv, ENrvAGIGILTNle, ENleAGIGILTV, ENleAGIGILTNrv, ENleAGIGILTNle, ELAGIGILTNle, EAAGIGILTNrv, and EAAGIGILTNle.

In another embodiment, the non-natural amino acid is selected from the group consisting of c3a [beta-cyclopropylalanine], c5g [aminocyclopentyl carboxylic acid], chg [L-cyclohexylglycine], cpg [L-cyclopentylglycine], dfb [L-6,6-difluoro-bicyclo[3.1.0]hexylglycine], dhl [L-isopropenealanine], phg [L-phenylglycine], and sta [L-styrylalanine].

As used herein, the "[c3a]" refers to the following chemical structures:

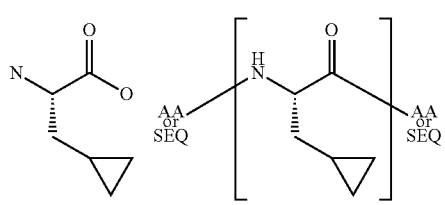

As used herein, the "[c5g]" refers to the following chemical structures:

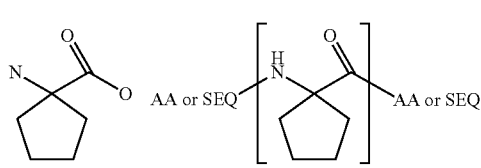

As used herein, the "[chg]" refers to the following chemical structures:

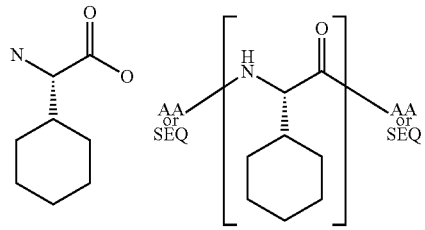

As used herein, the "[cpg]" refers to the following chemical structures:

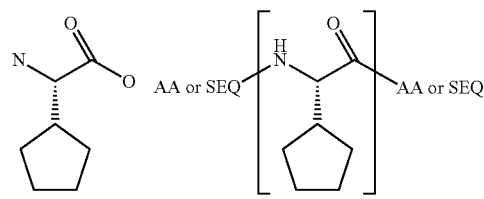

As used herein, the "[dfb]" refers to the following chemical structures:

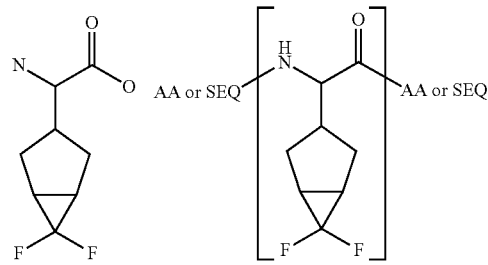

As used herein, the "[dhl]" refers to the following chemical structures:

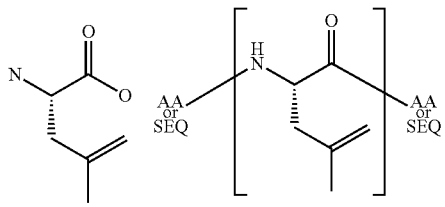

As used herein, the "[phg]" refers to the following chemical structures:

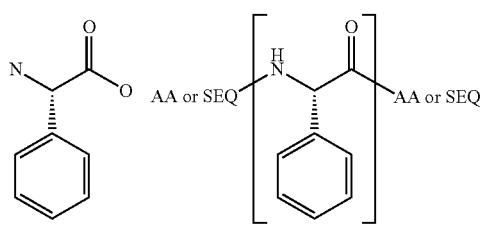

As used herein, the "[sta]" refers to the following chemical structures:

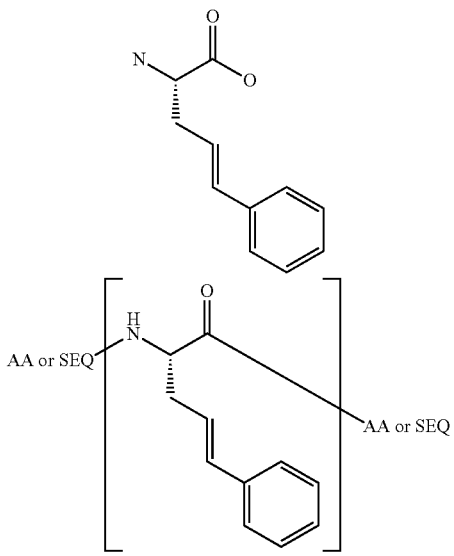

As used herein, the term "MHCI" means "Class I Major Histocompatibility Complex", and can be selected from those listed in Tables 6 and 7, below. As used herein, the term "HLA" refers to Human Leukocyte Antigen and is the name of the major histocompatibility complex (MHC) in humans. HLA is important in immune functions including the differentiation between self and non-self cells and antigen presentation.

As used herein to refer to a peptide, the term "wild type" refers to the amino acid sequence of a naturally occurring peptide. As used herein to refer to an amino acid residue, the term "wild type" refers to the amino acid residue that occurs naturally at a particular position in a naturally occurring peptide.

The "parent peptide" (also referred to herein as "parent epitope" and "MHC restricted antigen") is a putative MHCI epitope. Parent peptides can be identified using computer programs that make predictions based on the presence or absence of the conserved residues at both primary and secondary anchor sites. There are programs that consider all of the positions in a peptide to predict whether it is a MHCI peptide. Parent peptides can also be identified experimentally using peptides prepared synthetically and then tested for their ability to bind to the MHCI protein complex. Parent peptides may also be identified by extracting peptides from the MHC I molecules of a population of cells. See below for methods to identify parent peptides. It has also been verified experimentally that many naturally occurring MHCI epitopes do not have the consensus anchor residues.

The "parent peptide" can be any peptide, but preferably is a peptide obtained from, or otherwise identified as part of, synthesized by, or associated with, a target antigen of a cancer cell or infectious agent or a cell infected with an infectious agent (e.g., a peptide encoded by an infectious agent or a self-peptide whose expression is induced by the infectious agent). The parent peptide may be a peptide that occurs naturally, either by itself or as a portion of a larger protein molecule, i.e., a target antigen. A parent peptide may be a naturally occurring peptide (either by itself or as a portion of a target antigen), i.e., a "wild type" peptide, or a parent peptide may be an analog of a wild type peptide. The expression of the parent peptide (or the larger target antigen of which it may be part) may be unique to a cancer cell or to a particular infectious agent. Alternatively, the parent peptide (or the target antigen of which it may be part) may be expressed by both cancer and non-cancer cells in a subject, but may be relatively over-expressed by the cancer cells, or may be common to both the infectious agent and the subject, but may be relatively over-expressed by the infectious agent. Alternatively, the parent peptide may not be naturally occurring, but may be produced through one or more synthetic schemes. In either case, the term "parent peptide" will generally refer to the immediate precursor of a peptide derivative of the present invention prior to substitution with a non-natural amino acid, e.g., a conformation-constraining non-natural amino acid residue, according to the present invention.

The "parent peptide" and the "peptide derivative" of the present invention are identical except for the substitution of one or more non-natural amino acids as described above (e.g., at P2 and/or at P6 or P7 or PΩ for HLA-A2). The parent peptide may or may not have the amino acid sequence of a wild type (i.e., naturally occurring) peptide. For example, a peptide having a wild type amino acid sequence may be directly modified according to the present invention to replace the native amino acid residue at the P2 position with a non-natural amino acid, in which case the wild type peptide is the "parent peptide" of the peptide derivative. Alternatively, a peptide having a non-wild type amino acid sequence (referred to herein as an analog) may be modified according to the present invention to substitute a non-natural amino acid for the amino acid residue at, e.g., the P2 position, in which case a non-wild type peptide is the "parent peptide" of the peptide derivative. An example of a non-natural peptide (analog), which may be a parent peptide in the present methods, is a heteroclitic analog, e.g., as described in US 20060018915 A1.

The term "anchor position" refers to certain amino acid positions within a peptide that bind to a MHCI molecule where one or a small number of amino acid residues are found almost exclusively, i.e., they are conserved or semi-conserved across a population of epitopes. The amino acids in these positions are said to "anchor" the peptide into the binding groove of the MHCI molecule by having side chains that are complementary to pockets present in the binding groove. One of these pockets usually binds the carboxy-terminal amino acid of a 8, 9, 10, or 11 amino acid long peptide. The other positions of the anchor residues are different between the MHCI alleles, but frequently are the second, third or fifth residue from the amino terminus (see, e.g., Tables 6 and 7, below). For peptides that bind to HLA-A2.1, the anchor residues are at positions P2 (i.e., position 2 numbering sequentially from the amino terminal amino acid) and PΩ (the carboxy-terminal position that can either be P9 (position 9) or P10 (position 10), depending on the length of the peptide).

Peptide derivatives can be designed according to the methods of the invention from a parent peptide, without regard to the MHC binding motif or supermotif to which the parent peptide belongs. The primary anchor residues of the HLA class I peptide epitope supermotifs and motifs are summarized below. In some cases, peptides may be listed in both a motif and a supermotif summary. The relationship of a particular motif and respective supermotif is indicated in the description of the individual motifs.

i. HLA-A1 Supermotif

The HLA-A1 supermotif is characterized by the presence in peptide ligands of a small (T or S) or hydrophobic (L, I, V, or M) primary anchor residue in position 2, and an aromatic (Y, F, or W) primary anchor residue at the C-terminal position of the epitope. The corresponding family of HLA molecules that bind to the A1 supermotif (i.e., the HLA-A1 supertype) is comprised of at least A*0101, A*2601, A*2602, A*2501, and A*3201 (see, e.g., DiBrino, M. et al., J. Immunol. 151:5930, 1993; DiBrino, M. et al., J. Immunol. 152:620, 1994; Kondo, A. et al., Immunogenetics 45:249, 1997).

ii. HLA-A2 Supermotif

Primary anchor specificities for allele-specific HLA-A2.1 molecules (see, e.g., Falk et al., Nature 351:290-296, 1991; Hunt et al., Science 255:1261-1263, 1992; Parker et al., J. Immunol. 149:3580-3587, 1992; Ruppert et al., Cell 74:929-937, 1993) and cross-reactive binding among HLA-A2 and -A28 molecules have been described. (See, e.g., Fruci et al., Human Immunol. 38:187-192, 1993; Tanigaki et al., Human Immunol. 39:155-162, 1994; Del Guercio et al., J. Immunol. 154:685-693, 1995; Kast et al., J. Immunol. 152:3904-3912, 1994 for reviews of relevant data.) These primary anchor residues define the HLA-A2 supermotif; which presence in peptide ligands corresponds to the ability to bind several different HLA-A2 and -A28 molecules. The HLA-A2 supermotif comprises peptide ligands with L, I, V, M, A, T, or Q as a primary anchor residue at position 2 and L, I, V, M, A, or T as a primary anchor residue at the C-terminal position of the epitope.

The corresponding family of HLA molecules (i.e., the HLA-A2 supertype that binds these peptides) is comprised of at least: A*0201, A*0202, A*0203, A*0204, A*0205, A*0206, A*0207, A*0209, A*0214, A*6802, and A*6901.

iii. HLA-A3 Supermotif

The HLA-A3 supermotif is characterized by the presence in peptide ligands of A, L, I, V, M, S, or T as a primary anchor at position 2, and a positively charged residue, R or K, at the C-terminal position of the epitope, e.g., in position 9 of 9-mers (see, e.g., Sidney et al., Hum. Immunol. 45:79, 1996). Exemplary members of the corresponding family of HLA molecules (the HLA-A3 supertype) that bind the A3 supermotif include at least A*0301, A*1101, A*3101, A*3301, and A*6801.

iv. HLA-A24 Supermotif

The HLA-A24 supermotif is characterized by the presence in peptide ligands of an aromatic (F, W, or Y) or hydrophobic aliphatic (L, I, V, M, or T) residue as a primary anchor in position 2, and Y, F, W, L, I, or M as primary anchor at the C-terminal position of the epitope (see, e.g., Sette and Sidney, Immunogenetics, 50:201-212, 1999). The corresponding family of HLA molecules that bind to the A24 supermotif (i.e., the A24 supertype) includes at least A*2402, A*3001, and A*2301.

v. HLA-B7 Supermotif

The HLA-B7 supermotif is characterized by peptides bearing proline in position 2 as a primary anchor, and a hydrophobic or aliphatic amino acid (L, I, V, M, A, F, W, or Y) as the primary anchor at the C-terminal position of the epitope. The corresponding family of HLA molecules that bind the B7 supermotif (i.e., the HLA-B7 supertype) is comprised of at least twenty six HLA-B proteins including: B*0702, B*0703, B*0704, B*0705, B*1508, B*3501, B*3502, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701, and B*7801 (see, e.g., Sidney, et al., J. Immunol. 154:247, 1995; Barber, et al., Curr. Biol. 5:179, 1995; Hill, et al., Nature 360:434, 1992; Rammensee, et al., Immunogenetics 41:178, 1995 for reviews of relevant data).

vi. HLA-B27 Supermotif

The HLA-B27 supermotif is characterized by the presence in peptide ligands of a positively charged (R, H, or K) residue as a primary anchor at position 2, and a hydrophobic (F, Y, L, W, M, I, A, or V) residue as a primary anchor at the C-terminal position of the epitope (see, e.g., Sette and Sidney, Immunogenetics, 50:201-212, 1999). Exemplary members of the corresponding family of HLA molecules that bind to the B27 supermotif (i.e., the B27 supertype) include at least B*1401, B*1402, B*1509, B*2702, B*2703, B*2704, B*2705, B*2706, B*3801, B*3901, B*3902, and B*7301.

vii. HLA-B44 Supermotif

The HLA-B44 supermotif is characterized by the presence in peptide ligands of negatively charged (D or E) residues as a primary anchor in position 2, and hydrophobic residues (F, W, Y, L, I, M, V, or A) as a primary anchor at the C-terminal position of the epitope (see, e.g., Sidney et al., Immunol. Today 17:261, 1996). Exemplary members of the corresponding family of HLA molecules that bind to the B44 supermotif (i.e., the B44 supertype) include at least: B*1801, B*1802, B*3701, B*4001, B*4002, B*4006, B*4402, B*4403, and B*4006.

viii. HLA-B58 Supermotif

The HLA-B58 supermotif is characterized by the presence in peptide ligands of a small aliphatic residue (A, S, or T) as a primary anchor residue at position 2, and an aromatic or hydrophobic residue (F, W, Y, L, I, V, M, or A) as a primary anchor residue at the C-terminal position of the epitope (see, e.g., Sette and Sidney, Immunogenetics, 50:201-212, 1999 for reviews of relevant data). Exemplary members of the corresponding family of HLA molecules that bind to the B58 supermotif (i.e., the B58 supertype) include at least: B*1516, B*1517, B*5701, B*5702, and B*5801.

ix. HLA-B62 Supermotif

The HLA-B62 supermotif is characterized by the presence in peptide ligands of the polar aliphatic residue Q or a hydrophobic aliphatic residue (L, V, M, I, or P) as a primary anchor in position 2, and a hydrophobic residue (F, W, Y, M, I, V, L, or A) as a primary anchor at the C-terminal position of the epitope (see, e.g., Sette and Sidney, Immunogenetics, 50:201-212, 1999). Exemplary members of the corresponding family of HLA molecules that bind to the B62 supermotif (i.e., the B62 supertype) include at least: B*1501, B*1502, B*1513, and B5201.

x. HLA-A1 Motif

The HLA-A1 motif is characterized by the presence in peptide ligands of T, S, or M as a primary anchor residue at position 2 and the presence of Y as a primary anchor residue at the C-terminal position of the epitope. An alternative allele-specific A1 motif is characterized by a primary anchor residue at position 3 rather than position 2. This motif is characterized by the presence of D, E, A, or S as a primary anchor residue in position 3, and a Y as a primary anchor residue at the C-terminal position of the epitope (see, e.g., DiBrino et al., J. Immunol., 152:620, 1994; Kondo et al., Immunogenetics 45:249, 1997; and Kubo et al., J. Immunol. 152:3913, 1994 for reviews of relevant data).

xi. HLA-A*0201 Motif

An HLA-A2*0201 motif was determined to be characterized by the presence in peptide ligands of L or M as a primary anchor residue in position 2, and L or V as a primary anchor residue at the C-terminal position of a 9-residue peptide (see, e.g., Falk et al., Nature 351:290-296, 1991) and was further found to comprise an I at position 2 and I or A at the C-terminal position of a nine amino acid peptide (see, e.g., Hunt et al., Science 255:1261-1263, Mar. 6, 1992; Parker et al., J. Immunol. 149:3580-3587, 1992). The A*0201 allele-specific motif has also been defined to additionally comprise V, A, T, or Q as a primary anchor residue at position 2, and M or T as a primary anchor residue at the C-terminal position of the epitope (see, e.g., Kast et al., J. Immunol. 152:3904-3912, 1994). Thus, the HLA-A*0201 motif comprises peptide ligands with L, I, V, M, A, T, or Q as primary anchor residues at position 2 and L, I, V, M, A, or T as a primary anchor residue at the C-terminal position of the epitope. The preferred and tolerated residues that characterize the primary anchor positions of the HLA-A*0201 motif are identical to the residues describing the A2 supermotif.

xii. HLA-A3 Motif

The HLA-A3 motif is characterized by the presence in peptide ligands of L, M, V, I, S, A, T, F, C, G, or D as a primary anchor residue at position 2, and the presence of K, Y, R, H, F, or A as a primary anchor residue at the C-terminal position of the epitope (see, e.g., DiBrino et al., Proc. Natl. Acad. Sci USA 90:1508, 1993; and Kubo et al., J. Immunol. 152:3913-3924, 1994).

xiii. HLA-A1 Motif

The HLA-A11 motif is characterized by the presence in peptide ligands of V, T, M, L, I, S, A, G, N, C, D, or F as a primary anchor residue in position 2, and K, R, Y, or H as a primary anchor residue at the C-terminal position of the epitope (see, e.g., Zhang et al., Proc. Natl. Acad. Sci USA 90:2217-2221, 1993; and Kubo et al., J. Immunol. 152: 3913-3924, 1994).

xiv. HLA-A24 Motif

The HLA-A24 motif is characterized by the presence in peptide ligands of Y, F, W, or M as a primary anchor residue in position 2, and F, L, I, or W as a primary anchor residue at the C-terminal position of the epitope (see, e.g., Kondo et al., J. Immunol. 155:4307-4312, 1995; and Kubo et al., J. Immunol. 152:3913-3924, 1994).

Parent peptides may be from any target antigen. Preferred target peptides are tumor-associated (TAA) or tumor-specific antigens (TSA) and antigens produced by an infectious agent or a host protein produced during infection. The term "target antigen" refers to any protein or peptide that, when introduced into a host having an immune system (directly or upon expression as in, e. g., DNA vaccines), is recognized by the immune system of the host and is capable of eliciting a specific immune reaction. The terms "tumor-associated antigen (TAA)" and "tumor-specific antigen (TSA)" are used interchangeably and refer to an antigenic peptide that is associated with a tumor or a cancerous cell. TAAs include, for example, mutated cellular proteins such as mutated tumor suppressor gene products, oncogene products (including fusion proteins), and foreign proteins such as viral gene products. Non-mutated cellular proteins may also be TAAs if they are expressed aberrantly (e. g., in an inappropriate subcellular compartment) or in supernormal quantities.

Examples of preferred target antigens include TAAs such as ErbB receptors, Melan A (MART1), gp100, tyrosinase, TRP-1/gp 75, and TRP-2 (in melanoma; for additional examples, see also a list of antigens provided in Storkus and Zarour, Forum (Genova), 2000 July-September, 10 (3): 256-270); MAGE-1 and MAGE-3 (in bladder, head and neck, and non-small cell carcinoma); HPV EG and E7 proteins (in cervical cancer); Mucin (MUC-1) (in breast, pancreas, colon, and prostate cancers); prostate-specific antigen (PSA) (in prostate cancer); carcinoembryonic antigen (CEA) (in colon, breast, lung, thyroid, and gastrointestinal cancers), P1A tumor antigen (e. g., as disclosed in International Patent Publication No. WO 98/56919), and such shared tumor-specific antigens as MAGE-2, MAGE-4, MAGE-6, MAGE-10, MAGE-12, BAGE-1, CAGE-1, 2, 8, CAGE-3 to 7, LAGE-1, NY-ESO-1/LAGE-2, NA-88, and GnTV (see, e. g., International Patent Publication No. WO 98/56919).

In a specific embodiment, the target antigen is carcinoembryonic antigen (CEA). CEA is associated with neoplasms of epithelial origin, including carcinomas of the gastrointestinal tract, breast, lung, and thyroid, and therefore, constructs of the invention that include CEA epitopes may be used to threat neoplasms of epithelial origin.

Other target antigens of the invention include but are not limited to (i) protozoan antigens such as those derived from *Plasmodium* spp., *Toxoplasma* spp., *Pneumocystis carinii*, *Leishmania* sp., and *Trypanosoma* spp.; (ii) viral protein or peptide antigens such as those derived from influenza virus (e. g., surface glycoproteins hemagluttinin (HA) and neuraminidase (NA) or the nucleoprotein (NP) as described in Bodmer et al., Cell, 52: 253, 1988 and Tsuji et al., J. Virol. 72:6907-6910, 1998 or NP CTL epitopes as described in Gould et al., J. Virol., 65:5401, 1991; Murata et al., Cell Immunol., 173:96-107, 1996, and PCT Application No. WO 98/56919); immunodeficiency virus, e. g., a simian immunodeficiency virus (SIV) antigen (e. g., SIV-env CTL epitope as disclosed in PCT Application No. WO 98/56919), or a human immunodeficiency virus antigen (HIV-1) such as gp120 CTL epitopes as disclosed, e. g., in PCT Application No. WO 98/56919, gp160, pl8 antigen (e. g., CD8+ T cell epitopes and gp41 CTL epitopes as disclosed, e. g., in PCT Application No. WO 98/56919, Gag p24 CD8+ T cell epitopes, Gag pl7 CD8+ T cell epitopes, Tat, Pol, Nef CTL epitopes as disclosed, e. g., in PCT Application No. WO 98/56919, and Env CTL epitopes as disclosed, e. g., in PCT Application No. WO 98/56919); herpesvirus, e. g., a glycoprotein, for instance, from feline herpesvirus, equine herpesvirus, bovine herpesvirus, pseudorabies virus, canine herpesvirus, herpes simplex virus (HSV, e. g., HSV tk, gB, gD), herpes zoster virus, Marek's Disease Virus, herpesvirus of turkeys (HVT), cytomegalovirus (CMV), or Epstein-Barr virus; hepatitis C virus; human papilloma virus (HPV);

human T cell leukemia virus (HTLV-1); bovine leukemia virus (e. g., gp51, 30 envelope antigen); feline leukemia virus (FeLV) (e. g., FeLV envelope protein, a Newcastle Disease Virus (NDV) antigen, e. g., HN or F); rous associated virus (such as RAV-1 env); infectious bronchitis virus (e. g., matrix and/or preplomer); flavivirus (e. g., a Japanese encephalitis virus (JEV) antigen, a Yellow Fever antigen, or a Dengue virus antigen); Morbillivirus (e. g., a canine distemper virus antigen, a measles antigen, or rinderpest antigen such as HA or F); rabies (e. g., rabies glycoprotein G); parvovirus (e. g., a canine parvovirus antigen); hepatitis C virus (HCV); poxvirus (e. g., an ectromelia antigen, a canary poxvirus antigen, or a fowl poxvirus antigen such as chicken pox virus varicella zoster antigen); infectious bursal disease virus (e. g., VP2, VP3, or VP4); Hantaan virus; mumps virus, and measles virus; (iii) bacterial antigens such as *Mycobacterium tuberculosis*-specific (e. g., *Bacillus* Calmette-Guerin (BCG)-38 kD protein; antigen 85 complex (as described in Klein et al., J. Infect. Dis., 183:928-34, 2001), see also a list of antigens in Klein and McAdam, Arch. Immunol. Ther. Exp. (Warsz.), 47: 313-320, 1999), *Listeria monocytoges*-specific (e. g., as disclosed in Finelli et al., Immunol. Res., 19: 211-223, 1999), *Salmonella typhii*-specific, *Shigella flexineri*-specific, *staphylococcus*-specific, *streptococcus*-specific, *pneumococcus*-specific (e. g., PspA (see PCT Publication No. WO 92/14488)), *Neisseria gonorrhea*-specific, *Borelia*-specific (e. g., OspA, OspB, OspC antigens of *Borrelia* associated with Lyme disease such as *Borrelia bergdorferi*, *Borrelia afzelli*, and *Borrelia garinii* (see, e.g., U.S. Pat. No. 5,523,089; PCT Application Nos. WO 90/04411, WO 91/09870, WO 93/04175, WO 96/06165, WO93/08306; PCT/US92/08697; Bergstrom et al., Mol. Microbiol., 3:479-486, 1989; Johnson et al., Infect. and Immun. 60:1845-1853, 1992; Johnson et al., Vaccine 13:1086-1094, 1995; The Sixth International Conference on Lyme Borreliosis: Progress on the Development of Lyme Disease Vaccine, Vaccine 13:133-135, 1995)), *A. pertussis*-specific, *S. parathyphoid* A and B-specific, *C. diphtheriae*-specific, *C. tetanus*-specific, *C. botulinum*-specific, *C. perfringens*-specific, *A. anthracis*-specific, *A. pestis*-specific, *V cholera*-specific, *H. influenzae*-specific, *T. palladium*-specific, *Chlamydia trachomatis*-specific (e. g., as disclosed in Kim et al., J. Immunol., 162: 6855-6866, 1999), and *pseudomonas*-specific proteins or peptides; and (iv) fungal antigens such as those isolated from *candida* (e. g., 65 kDa mannoprotein (MP65) from *Candida albicans*), *trichophyton*, or *pityrosporum*.

The foregoing list of target antigens is intended as exemplary, as the antigen of interest can be derived from any animal or human pathogen or tumor or cancerous cell. With respect to DNA encoding pathogen-derived antigens of interest, attention is directed to, e. g., U.S. Pat. Nos. 4,722,848; 5,174,993; 5,338,683; 5,494,807; 5,503,834; 5,505,941; 5,514,375; 5,529,780; U. K. Patent No. GB 2 269 820 B; and PCT Publication Nos. WO 92/22641; WO 93/03145; WO 94/16716; WO 96/3941; PCT/US94/06652. With respect to antigens derived from tumor viruses, reference is also made to Molecular Biology of Tumor Viruses, RNA Tumor Viruses, Second Edition, Edited by Weiss et al., Cold Spring Harbor Laboratory Press, 1982. For a list of additional antigens useful in the compositions of the invention see also Stedman's Medical Dictionary (24th edition, 1982).

Additional examples of target antigens include prostate specific antigens (PSA), melanoma antigens MAGE-1, MAGE-2, MAGE-3, MAGE-11, MAGE-A10, as well as BAGE, GAGE, RAGE, MAGE-C1, LAGE-1, CAG-3, DAM, MUC1, MUC2, MUC18, NY-ESO-1, MUM-1, CDK4, BRCA2, NY-LU-1, NY-LU-7, NY-LU-12, CASP8, RAS, KIAA-2-5, SCCs, p53, p73, CEA, Her 2/neu, Melan-A, gp100, tyrosinase, TRP2, gp75/TRP1, kallikrein, prostate-specific membrane antigen (PSM), prostatic acid phosphatase (PAP), prostate-specific antigen (PSA), PT1-1, β-catenin, PRAME, Telomerase, FAK, cyclin D1 protein, NOEY2, EGF-R, SART-1, CAPB, HPVE7, p15, Folate receptor CDC27, PAGE-1, and PAGE-4.

Additional examples of target antigens include hepatitis B core and surface antigens (HBVc, HBVs), hepatitis C antigens, Epstein-Barr virus antigens, human immunodeficiency virus (HIV) antigens and human papilloma virus (HPV) antigens, *Mycobacterium tuberculosis* and *Chlamydia*. Examples of suitable fungal antigens include those derived from *Candida albicans*, *Cryptococcus neoformans*, *Coccidoides* spp., *Histoplasma* spp, and *Aspergillus fumigatis*. Examples of suitable protozoan parasitic antigens include those derived from *Plasmodium* spp., including *P. falciparum*, *Trypanosoma* spp., *Schistosoma* spp., *Leishmania* spp and the like.

In a non-limiting embodiment, the parent peptide from which a peptide derivative of the present invention can be prepared is selected from the group consisting of an HLA-A0201-restricted peptide from a universal tumor antigen. In a non-limiting embodiment, the parent peptide is selected from Survivin, hTERT and CYP1B1. In another non-limiting embodiment, the parent peptide is an HLA-A0201-restricted MART-1 peptide.

In a non-limiting embodiment, peptide derivatives provided by the present invention are based on the MART-1 peptide epitope of Melan-A, the amino acid sequence of which is AAGIGILTV (SEQ ID NO:1). Such a MART-1-based peptide derivative can be based on the 9-mer (nonamer) parent amino acid sequence AAGIGILTV (SEQ ID NO:1); or on the 10-mer (decamer) parent amino acid sequence EAAGIGILTV (SEQ ID NO:2).

In one non-limiting embodiment, the present invention provides peptide derivatives based on the parent or wild type MART-1 nonamer sequence AAGIGILTV (SEQ ID NO:1), wherein the peptide derivatives have a substitution at a position corresponding to amino acid Position 2 (P2) in the nonamer peptide (as numbered from the amino terminus of the nonamer peptide), such that the alanine residue present at P2 of the wild type nonamer peptide is replaced with a non-natural amino acid. Such "nonamer" peptide derivatives of the present invention have the general formula A-$X_{aa}$-GIGILTV (SEQ ID NO:3), where $X_{aa}$ represents a non-natural amino acid. In one embodiment, the non-natural amino acid has increased conformational constraint compared to the conformational constraint present in the original amino acid at P2 in parent peptide AAGIGILTV (SEQ ID NO:1). In some embodiments, the derivative peptide that results from the introduction of the non-natural amino acid has an increased conformational constraint compared to the parent peptide. Such substitution at P2 of this wild type nonamer sequence serves to provide "MART-1-based peptide derivatives" having at least one, or at least two, or at least three, or at least four, or all five, of the aforementioned properties.

Specific non-limiting embodiments of such MART-1-based peptide derivatives include:

(a)
A-[c3a]-GIGILTV; (SEQ ID NO: 4)

(b)
A-[c5g]-GIGILTV; (SEQ ID NO: 5)

(c)
A-[chg]-GIGILTV; (SEQ ID NO: 6)

(d)
A-[cpg]-GIGILTV; (SEQ ID NO: 7)

(e)
A-[dfb]-GIGILTV; (SEQ ID NO: 8)

(f)
A-[dhl]-GIGILTV; (SEQ ID NO: 9)

(g)
A-[phg]-GIGILTV; (SEQ ID NO: 10)
and (h)
A-[sta]-GIGILTV. (SEQ ID NO: 11)

In another non-limiting embodiment, the present invention provides peptide derivatives based on the parent or wild type MART-1 decamer sequence EAAGIGILTV (SEQ ID NO:2), wherein the peptide derivatives have a substitution at a position corresponding to amino acid Position 2 (P2) in the decamer peptide (as numbered from the amino terminus of the decamer peptide), such that the alanine residue present at P2 of the wild type decamer peptide is replaced with a non-natural amino acid. Such "decamer" peptide derivatives of the present invention have the general formula E-$X_{aa}$-AGIGILTV (SEQ ID NO:12), where $X_{aa}$ represents a non-natural amino acid. In some embodiments, the non-natural amino acid has increased conformational constraint in the peptide derivative compared to the conformational constraint of the original amino acid in the wild type decamer peptide EAAGIGILTV (SEQ ID NO:2). In some embodiments, the derivative peptide that results from the introduction of the non-natural amino acid has an increased conformational constraint compared to the parent peptide. Such substitution at P2 of this wild type decamer sequence thus serves to provide additional "MART-1-based peptide derivatives" having at least one, or at least two, or at least three, or at least four, or all five of the aforementioned properties.

Specific non-limiting embodiments of such MART-1-based peptide derivatives include:

(a)
E-[c3a]-AGIGILTV; (SEQ ID NO: 13)

(b)
E-[c5g]-AGIGILTV; (SEQ ID NO: 14)

(c)
E-[chg]-AGIGILTV; (SEQ ID NO: 15)

(d)
E-[cpg]-AGIGILTV; (SEQ ID NO: 16)

(e)
E-[dfb]-AGIGILTV; (SEQ ID NO: 17)

(f)
E-[dhl]-AGIGILTV; (SEQ ID NO: 18)

(g)
E-[phg]-AGIGILTV; (SEQ ID NO: 19)
and (h)
E-[sta]-AGIGILTV. (SEQ ID NO: 20)

In another non-limiting embodiment, peptide derivatives provided by the present invention are based on a peptide selected from the Survivin protein (GenBank #U75285; Reed, J. C., 2001, J. Clin. Invest. 108: 965-969). The Survivin protein is a member of the inhibitors of apoptosis gene family, which suppresses apoptosis and regulates cell division (Reed, J. C., 2001, J. Clin. Invest. 108: 965-969). The Survivin protein appears to preferentially inhibit mitochondrial-dependent apoptosis by targeting caspase-9 and plays a critical role in mitosis and embryonic development. Multiple splice variants of Survivin have been identified (Mahotka, C, et al, 1999, Cancer Res. 59, 6097-6102; Badran, A, et al, 2004, Biochem. Biophys. Res. Commun. 314, 902-907), but the functional significance of these variants has not been established. Survivin is among the most tumor-specific of all human gene products and over-expression has been documented in many of the major tumor types. In addition, over-expression of Survivin in cancer patients has been correlated with a more aggressive disease and poor survival.

In one non-limiting embodiment, peptide derivatives of the present invention are based on the parent or wild type Survivin nonamer sequence ISTFKNWPF (SEQ ID NO:21), wherein the peptide derivatives have a substitution at amino acid Position 2 (P2) (as numbered from the amino terminus of the nonamer peptide), such that the serine residue present at position P2 of the wild type nonamer peptide is replaced with a non-natural amino acid. Such "nonamer" peptide derivatives have the general formula I-$X_{aa}$-TFKNWPF (SEQ ID NO:22), where $X_{aa}$ is a non-natural amino acid. In some embodiments, the non-natural amino acid has increased conformational constraint in the peptide derivative compared to the conformational constraint of the original amino acid in the nonamer peptide ISTFKNWPF (SEQ ID NO:21). In some embodiments, the derivative peptide that results from the introduction of the non-natural amino acid has an increased conformational constraint compared to the parent peptide. Such substitution at P2 of this wild type nonamer sequence serves to provide "Survivin-based peptide derivatives" having at least one, or at least two, or at least three, or at least four, or all five of the aforementioned properties.

Specific non-limiting embodiments of such Survivin-based peptide derivatives include:

(a)
I-[c3a]-TFKNWPF; (SEQ ID NO: 23)

(b)
I-[c5g]-TFKNWPF; (SEQ ID NO: 24)

(c)
I-[chg]-TFKNWPF; (SEQ ID NO: 25)

(d)

I-[cpg]-TFKNWPF; (SEQ ID NO: 26)

(e)

I-[dfb]-TFKNWPF; (SEQ ID NO: 27)

(f)

I-[dhl]-TFKNWPF; (SEQ ID NO: 28)

(g)

I-[phg]-TFKNWPF; (SEQ ID NO: 29)
and (h)

I-[sta]-TFKNWPF. (SEQ ID NO: 30)

In another non-limiting embodiment, the present invention provides peptide derivatives based on the wild type Survivin nonamer sequence of KVRRAIEQL (SEQ ID NO:31), wherein the peptide derivatives have a substitution at a position corresponding to amino acid Position 2 (P2) in this nonamer peptide (as numbered from the amino terminus of the decamer peptide), such that the valine residue present at P2 of the wild type nonamer peptide is replaced with a non-natural amino acid. Such "nonamer" peptide derivatives of the present invention have the general formula K-$X_{aa}$-RRAIEQL (SEQ ID NO:32), where $X_{aa}$ represents a non-natural amino acid. In some embodiments, the non-natural amino acid has increased conformational constraint in the peptide derivative compared to the conformational constraint present in the original amino acid in the wild type nonamer peptide KVRRAIEQL (SEQ ID NO:31). In some embodiments, the derivative peptide that results from the introduction of the non-natural amino acid has an increased conformational constraint compared to the parent peptide. Such substitution at P2 of this wild type nonamer sequence serves to provide additional "Survivin-based peptide derivatives" having at least one, or at least two, or at least three, or at least four, or all five of the aforementioned properties.

Specific non-limiting embodiments of such Survivin-based peptide derivatives include:

(a)

K-[c3a]-RRAIEQL; (SEQ ID NO: 33)

(b)

K-[c5g]-RRAIEQL; (SEQ ID NO: 34)

(c)

K-[chg]-RRAIEQL; (SEQ ID NO: 35)

(d)

K-[cpg]-RRAIEQL; (SEQ ID NO: 36)

(e)

K-[dfb]-RRAIEQL; (SEQ ID NO: 37)

(f)

K-[dhl]-RRAIEQL; (SEQ ID NO: 38)

(g)

K-[phg]-RRAIEQL; (SEQ ID NO: 39)
and (h)

K-[sta]-RRAIEQL. (SEQ ID NO: 40)

Any peptide derivative provided by the present invention can optionally further comprise one or more other modifications so as to: (i) further improve one, or two, or three, or four, or all five of the aforementioned properties obtained by the single substitution alone as described above and/or (ii) improve a different property than the one or more of the aforementioned properties obtained by the single substitution alone as described above. For example, the peptide derivative prepared as described above can further comprise a substitution of a second naturally occurring amino acid residue in the parent peptide with the same or different non-natural amino acid as used in the first substitution.

In a non-limiting example, a peptide derivative of the present invention can incorporate a second substitution. Such a second substitution may be at a second primary anchor position or another position in the parent peptide. Such a second substitution may be at Position 6 (P6), at Position 7 (P7), or at Position Omega (PΩ), which is the amino acid residue occupying the last position at the carboxyl end of the peptide. As with the first amino acid substitution described above, the second amino acid substitution can serve to replace a naturally occurring amino acid residue in the peptide with a non-natural amino acid, such as a conformation constraining non-natural amino acid residue. For example, the amino acid residue at PΩ in the peptide can be substituted with a conformation constraining non-natural amino acid residue to further increase the conformational constraint within the peptide derivative.

In a non-limiting embodiment, a general formula for a peptide derivative of the present invention based on a nonamer MART-1 peptide and having a double substitution is A-$X_{aa1}$-GIG-$X_{aa2}$-LTV (SEQ ID NO:41).

In another non-limiting embodiment, a general formula for a peptide derivative of the present invention based on a nonamer MART-1 peptide and having a double substitution is A-$X_{aa1}$GIGI-LT-$X_{aa2}$ (SEQ ID NO:42).

In another non-limiting embodiment, a general formula for a peptide derivative of the present invention based on a decamer MART-1 peptide and having a double substitution is E-$X_{aa1}$-AGIG-$X_{aa2}$-LTV (SEQ ID NO:43), in a specific embodiment it is E-[c5g]-AGIG-[amv]-LTV (SEQ ID NO:49).

In another non-limiting embodiment, a general formula for a peptide derivative of the present invention based on a decamer MART-1 peptide and having a double substitution is E-$X_{aa1}$-AGIGILT-$X_{aa2}$ (SEQ ID NO:44).

In another non-limiting embodiment, a general formula for a peptide derivative of the present invention based on a nonamer Survivin peptide sequence and having a double substitution is I-$X_{aa1}$TFK-$X_{aa2}$-WPF (SEQ ID NO:45).

In another non-limiting embodiment, a general formula for a peptide derivative of the present invention based on a nonamer Survivin sequence and having a double substitution is I-$X_{aa1}$-TFKNWP-$X_{aa2}$ (SEQ ID NO:46).

In another non-limiting embodiment, a general formula for a peptide derivative of the present invention based on a nonamer Survivin peptide and having a double substitution is K-$X_{aa1}$-RRA-$X_{aa2}$-EQL (SEQ ID NO:47).

In another non-limiting embodiment, a general formula for a peptide derivative of the present invention based on a nonamer Survivin peptide and having a double substitution is K-X$_{aa1}$-RRAI-EQ-X$_{aa2}$ (SEQ ID NO:48).

In each of the above cases, each of X$_{aa1}$ and X$_{aa2}$ is independently selected from non-natural amino acids such as those that can provide increased conformational constraint in the particular peptide compared to the conformational constraint present in the parent peptide.

A peptide derivative of the invention may comprise additional changes from a wild type peptide. Such changes include replacement of a primary or secondary anchor residue with a conserved or semi-conserved residue at that position. Likewise, a peptide derivative of the invention may have a replacement of an amino acid at a non-anchor position with another amino acid, as described in US 20060018915 A2 to form a heteroclitic analog. Combinations of such replacements may be made in the wild type peptide to form an analog. Then, one or more amino acids of the analog are replaced with a non-natural amino acid to form a peptide derivative of the invention. Alternatively, a peptide derivative may be made that only contains the non-natural amino acid(s) of the invention, and then further modifications are made in the peptide derivative to form a peptide derivative containing, e.g., a conservative or semi-conservative substitution at an anchor position or a heteroclitic substitution.

Parent peptides and peptide derivatives of the present invention can be synthesized by any method known in the art of protein chemistry. The present invention does not require that a peptide derivative of the present invention be synthesized directly from a parent peptide as substrate to be converted to the peptide derivative. Instead, a peptide derivative of the present invention will most conveniently be prepared by de novo synthesis using, e.g., a commercially available peptide synthesizer.

The term "subject" as used herein refers to an animal having an immune system, preferably a mammal such as a rodent (e.g., mouse or rat), a companion animal (dog or cat), or a primate, and particularly a human.

The terms "therapeutically effective amount" and "therapeutically effective dose" refer to that quantity of a peptide derivative or pharmaceutical composition of the present invention that is sufficient to induce an immune response upon administration to a subject in need thereof or upon contacting a cell(s). As used herein with respect to pharmaceutical compositions, the terms "therapeutically effective amount" and "therapeutically effective dose" (used interchangeably with the term "immunogenetically effective amount" or "immunogenetically effective dose") refer to the amount or dose of a peptide derivative or pharmaceutical composition of the present invention sufficient to produce an effective immune response upon administration to a subject or upon contacting a cell(s).

For methods of treating a cancer, a "therapeutically effective dose" is an amount or dose of the peptide derivative or pharmaceutical composition of the present invention sufficient to produce an anti-cancer immune response in vivo useful to slow or reverse the progression of the cancer, or to reduce the severity of at least one symptom of the cancer.

For methods of preventing a cancer, a "therapeutically effective dose" is an amount or dose of the peptide derivative or pharmaceutical composition of the present invention sufficient to produce an anti-cancer immune response in vivo useful to prevent the onset of the cancer in, e.g., a subject prone to developing such a cancer as determined, e.g., by a diagnostic test or in view of a prior family history of cancer.

For methods of treating a pathogen-specific infection, a "therapeutically effective dose" is an amount or dose of the peptide derivative or pharmaceutical composition of the present invention sufficient to produce an immune response in vivo against that pathogen, which immune response is useful to slow or reverse the progression of the infection.

For methods of preventing a pathogen-specific infection, a "therapeutically effective dose" is an amount or dose of the peptide derivative or pharmaceutical composition of the present invention sufficient to produce an immune response in vivo against that pathogen, which immune response is useful to prevent the infection or preemptively to reduce the severity of infection produced by the pathogen.

4.2. Approach

The present invention provides a peptide derivative that is an MHC class I ("MHCI") restricted antigen, and which is prepared or derived from a parent peptide of 8 to 11 amino acid residues in length, and preferably either 9 or 10 amino acid residues in length, wherein the peptide derivative contains a non-natural amino acid substituted in place of a naturally occurring amino acid residue at one or more primary anchor positions, preferably at two primary anchor positions, and more preferably at one primary anchor position. Thus, the invention provides a peptide derivative of a MHCI restricted parent antigen (e.g., parent peptide or parent epitope) comprising a non-natural amino acid in at least one anchor position.

The invention further provides a peptide derivative of a MHCI restricted parent antigen comprising a non-natural amino acid at one anchor position and a second substitution at a second position. The second substitution at a second position may be at a second anchor position, or may be at the C-terminus (PΩ), e.g., for MHCI-peptides that do not have an anchor position at the C-terminus, or may be at position 6 (P6) or position 7 (P7).

A goal of the present invention is to create a streamlined, rational process by which to modify parent peptides (naturally occurring (i.e., wild type) peptide epitopes and relevant analogs) to create novel modified peptide molecules (peptide derivatives) that will more effectively stimulate the immune system to actively recognize and destroy cancer cells. These peptide derivatives are useful in certain pharmaceutical compositions and methods of the present invention to treat or prevent a cancer in a subject.

This rational process can also be used to modify parent peptides (wild type peptide epitopes and other relevant parent peptides) to create novel peptide derivatives that will stimulate the immune system to actively recognize and destroy infected cells. These peptide derivatives are useful in certain pharmaceutical compositions and methods of the present invention to treat or prevent an infection in a subject.

Previous methods for selecting other types of improved peptide epitopes utilized either: (i) prediction algorithms, which scan the target protein and predict which peptides would be epitopes based on the presence of specific residues at specific positions; or (ii) naturally immunized T-cell populations and peptide libraries to identify epitopes by directly testing for naturally occurring reactive T-cells.

A central aspect of the present invention is the replacement of at least one amino acid residue in an anchor position in the parent peptide with a non-natural amino acid. In some embodiments, the non-natural amino acid introduces increased conformational constraint into the peptide molecule. The present invention achieves peptide derivatives with improved immunogenicity, via, e.g., improved binding affinity or slowing of the kinetic off-rate from an MHCI (e.g., HLA-A2). Unlike approaches based on the high throughput screening of thousands or millions of compounds, the present invention typically provides optimized antigenic sequences by synthesizing less than 100 total compounds for any given parent sequence.

To demonstrate the effectiveness of this approach, several peptide derivatives were prepared by substituting one of several different non-natural amino acid residues into an anchor position of the MART-1 peptide, and these were tested using HLA-A0201, as described in the Examples below. Each non-natural amino acid substituted into the anchor positions was selected to impose a conformational constraint in the resulting peptide, leading to enhanced binding affinity of the peptide derivative to MHCI and increased stability of the MHCI-peptide derivative complex. These peptide derivatives were more potent than the wild type MART-1 peptide at inducing a CTL response, and displayed enhanced activity in T-cell assays. When used in in vitro education (IVE) experiments, the peptide derivatives are more efficient in expanding peptide specific T-cells, and the expanded T-cells recognize the wild type sequence, as demonstrated by ELISPOT assays. Such expanded T-cells would also be expected to recognize the wild type sequence in CTL lysis assays that are known in the art. Additionally, peptide-binding assays have been used to directly measure the affinities and off-rates of the peptide derivatives, demonstrating that these binding parameters can be selectively influenced. Thus, through the synthesis of fewer than 40 conformationally constrained peptides, several peptide derivatives based on the MART-1 epitope have been identified displaying higher affinity and similar or superior immunogenicity to the altered peptide ligand ("APL") MART-1 peptide. Using the same approach, novel peptide derivatives based on the Survivin protein have also been identified, as disclosed herein.

The present invention is thus based on two unexpected results. Firstly, the replacement of the consensus amino acid at an anchor position of the peptide (e.g., replacement of Leu at P2 of an HLA-A0201-restricted peptide) by a non-natural amino acid (such as an appropriate conformation constraining non-natural amino acid) can result in an increase in MHC-peptide affinity. Secondly, such increased affinity can result in increased immunogenicity of the peptide derivative compared to the wild type peptide in T-cell assays such as T-cell proliferation, cytokine production and cell lysis assays or other assays described herein or known in the art.

To identify a suitable parent peptide, a number of methods may be used, such as computational methods like SYFPEITHI (Rammensee, H. G., et al. (1997) "MHC Ligands and Binding Motifs" Landes Bioscience, Georgetown), BIMAS (Parker, K. C., et al. (1994) J. Immunol. 152, 163-175), artificial neural networks (Bredenbeck, A., et al. (2005) J. Immunol. 174, 6716-6724), and PePSSI (Bui, H. H., et al. (2006) Proteins 63, 43-52); and experimental methods using peptide libraries (Rodda, S. J. (2002) J. Immunological Methods 267, 71-77; Sospedra, M., et al. (2003) Methods 29, 236-247; Pinilla, C., et al. (2001) Cancer Res. 61, 5153-5160), and mass spectroscopy (Lemmel, C. and Stevanovic, S. (2003) Methods 29, 248-259; Lawendowski, C. A., et al. (2002) J. Immunol. 169, 2414-2421).

In some embodiments, the present invention involves directly measuring the affinity of the MHCI-peptide interaction using a library of candidate peptides and selecting from the library those peptides that show intermediate to moderately weak binding affinity for the MHCI of interest. One widely used method for measuring the binding affinity of peptides to MHCI is to perform a competition-based peptide-binding assay in which the inhibition of binding of a fixed concentration of a radiolabelled standard peptide is measured in the presence of varying concentrations of a test peptide (Ruppert, J., et al. (1993) Cell 74, 929-937; Sette, A., et al. (1994) J. Immunol. 153, 5586-5592; Bullock, T. N. J., et al. (2000) J. Immunol. 164, 2354-2361). In some embodiments, the relative affinity of a peptide binding to MHCI can be measured using cells deficient in TAP (transporter associated with antigen processing) which leads to expression on the cell surface of MHCI complexes without a bound peptide (Rock, K. L. and Goldberg, A. L. (1999) Annu. Rev. Immunol. 17, 730-779). As in the previous assay, binding affinity is measured relative to a standard peptide (Gross, D-A., et al. (2004) J. Clin. Invest. 113, 425-433).

Using the competition-based peptide-binding assay, candidate parent peptides have been classified into four categories: good binders with a $K_D \leq 50$ nM, intermediate binders with a $K_D$ of 50 to 500 nM, weak binders with a $K_D$ of 500 nM to 50 uM, and non-binders with a $K_D > 50$ uM (Ruppert, J., et al. (1993) Cell 74, 929-937; Sette, A., et al. (1994) J. Immunol. 153, 5586-5592). Further studies have been performed in which peptide binding affinity has been correlated with immunogenicity tested by measuring cytotoxic T cell responses. In these studies, all peptides that bind to MHCI with high affinity ($K_D \leq 50$ nM) are immunogenic, only some peptides that bind with intermediate affinity (50 to 500 nM) are immunogenic, and none of the peptides that bind with weak affinity (500 nM to 50 uM) are immunogenic (Sette, A., et al. (1994) J. Immunol. 153, 5586-5592; van der Burg, S. H., et al. (1996) J. Immunol. 156, 3308-3314). Exceptions to these correlations have been identified, but they appear to occur only rarely. These categories, based on peptide binding affinities, can be used to guide the selection of preferred candidate parent peptides where the preferred candidates would be those that bind to MHCI with intermediate to moderately weak affinity. Peptides with high binding affinity (good binders) most likely would not be selected since it is more likely that these self-peptides would not be immunogenic in patients due to selective elimination of T cells by thymic education and/or T cell tolerance. Parent peptides that bind with weak affinity would also not be preferred since there is a higher likelihood that these peptides would not be displayed on the surface of target cells. In addition, the stability of the MHCI-peptide complex has also been found to affect the immunogenicity of peptides (van der Burg, S. H., et al. (1996) J. Immunol. 156, 3308-3314). Consequently, measurements of MHCI-peptide complex stability are also important in the selection of preferred candidate parent peptides with complex half-lives greater than 3 hours correlating better with immunogenicity.

To implement this method, in some embodiments, a TAA or other target antigen is selected from which to identify one or more peptides of potential interest, and such peptides are used to prepare one or more potential derivative peptides for testing. The target antigen can be obtained from any cancer cell or pathogenic organism or infected cell from which a peptide can be selected for use in preparing a peptide derivative of the present invention useful to treat or prevent a condition or disorder in a subject in need of such treatment or prevention.

A candidate parent peptide may also be selected from a library. A library of peptides of 8, 9, 10 or 11 contiguous residues of the target antigen is constructed by any convenient method known in the art such as, e.g., by routine solid phase synthesis methods. The library may be of uniform size or mixed. Preferably the library is a "complete library" consisting of all possible such peptides of a specific size. The size of a library depends upon the length of the target protein and the length of the library's peptides. For example, a complete library of 10-mers of a 250-residue target will contain 240 peptides. A representative library consisting of at least a tenth of the members of the complete library can also be used. The library may be "edited" to exclude certain peptides such as those that might cause chemical instability (e.g., those containing cysteines and methionines), or that would be practically insoluble.

After the library is constructed, peptides having intermediate to moderately weak affinity for MHCI are identified as candidate parent peptides for further analysis. Parent peptides will preferably have a MHCI binding affinity value above 50 nM, but preferably below 50 uM as discussed above. Different screening methods can be used including the competition-based peptide-binding assay and the cell-based binding assay using TAP deficient cells. However, if the binding affinity ranges are used to select peptides, it will be important to use the same peptide binding assay or to run sufficient controls to correlate the results from the alternative assay with the competition-based peptide-binding assay cited herein.

Candidate parent peptides may also be known peptides chosen on the basis of published binding data or on the basis of analysis using an algorithm, or both, as noted above.

Once a peptide is identified as a candidate parent peptide for modification, a modified peptide can be constructed by substituting an amino acid residue at an anchor position in the peptide with a non-natural amino acid (e.g., conformation constraining non-natural amino acid), and the modified peptide tested for extent of cross-reactivity by the activated T-cells on the desired target cell. If a wild type residue at an anchor position is the most highly conserved residue, then the replacement may be selected from among non-natural amino acids chemically similar to the most highly conserved residue. If the wild type residue at the anchor position is not the most highly conserved residue, then it may be replaced with non-natural amino acids chemically similar to the most highly conserved residue. For example, a parent peptide may be a HLA-A2 peptide with an amino acid other than Leu at P2. A peptide derivative of this parent peptide may be a peptide that contains a non-natural peptide that is chemically similar to Leu, such as α-methyl leucine at P2. A peptide derivative prepared according to the method of, and suitable for practicing the present invention preferably displays an affinity value of less than 500 nM, and more preferably less than 50 nM to increase the likelihood that the peptide derivative will be immunogenic and elicit an immune response in patients when used as a component in a vaccine.

Screening for evaluation of MHCI-peptide affinity or MHCI-peptide complex stability can be performed by any known method. Such methods can be divided into cell-free methods, e.g., using isolated, recombinantly-produced MEW products (see section 5.1 in the Examples; Sette. A. et al. (1994) Mol. Immunol. 31:813-22; and Chen, Y. et al. (1994) J. Immunol. 152:2874-81), and cell-based methods (e.g., using MHCI produced by cells lacking a functional peptide transporter enzyme, which therefore do not form MHCI complexes with endogenous peptides). Valmori, D., et al., J. Immunol. 161, 6956-6962 (1998); Sarobe, et al., J. Clin. Invest. 102, 1239-1248 (1998); Gross, D-A., et al., J. Clin Invest. 113, 425-433 (2004). See section 5.1 in the Examples.

A method for measuring peptide binding affinity to isolated MHCI is reported in Sette, A., 1994, Mol. Immunology 31, 813-22. Those skilled in the art will appreciate that the calculated affinity based on measured on-rates and off-rates is dependent, to some extent, on technical factors, with temperature as one of the most sensitive. Because peptide-free MHCI products are unstable at 37° C., binding affinity is conventionally measured at 23° C. Hereafter, when stated as a limitation, binding affinity in a cell free assay will refer to the numerical value that would be obtained according to the method of Sette et al., at 23° C. Values determined by different assay methods and under different conditions may not be directly comparable to values determined using the method of Sette et al., so controls must be used that allow comparisons on relative terms, i.e., a given derivative is more or less potent than a given control.

Cell-based screening assays utilizing a cell line lacking a functional peptide transporter enzyme can be divided into two types: (i) affinity assays, and (ii) stability assays. In an example of an affinity assay, TAP-deficient cells are incubated overnight with a particular test peptide, washed, and the amount of the relevant MHCI-peptide complex found on their surface analyzed as a function of peptide concentration. Sarobe et al., J. Clin. Invest. 102:1239-48 (1998); and Gross et al., J. Clin. Invest. 113:425-33 (2004). The concentration required to provide some fraction of maximum display is proportional to the binding affinity of the peptide to MHCI. The results are typically reported as relative affinity where the binding of the test peptide is compared to the binding of a standard peptide that has been shown to typically bind with high affinity to MHCI ($K_D \leq 50$ nM (Ruppert, J., et al. (1993) Cell 74, 929-937; Sette, A., et al. (1994) J. Immunol. 153, 5586-5592).

In an example of a stability assay, cells are incubated with or without excess peptide overnight, the cells are washed free of unbound peptide, and then subjected to a pharmacologic blockade (e.g., with Brefeldin (Sigma-Aldrich)) of the expression of newly synthesized MHC. The amount of relevant cell-surface MHC can be measured at time points following institution of the blockade. Results from stability assays are often reported as $DC_{50}$ (dissociation complex) values, which is the time required for the loss of 50% of the MHCI/peptide complexes that were present on the surface of the cells at t=0. Typically, the time to reach half maximum binding for high affinity peptides is greater than 8 hours.

The stability assay is considered a measure of the "off-rate" of the peptide from the MHC-peptide complex, while affinity is affected by both the "on-rate" and the "off-rate". There are theoretical grounds for considering the "off-rate" the more important factor for determining the effective activity of an antigen, which has had some empirical support. Vertuani, S., et al., 2004, J. Immunol. 172, 3501-8. For the present invention, this distinction is not critical. Screening can be performed either by affinity or stability assays. Those skilled in the art will appreciate that technology specially adapted for the measurement of MHC-peptide complex interactions can be employed with particular advantage in the practice of the present invention. See U.S. Pat. No. 5,635,363 and No. 5,723,584. Useful technology is also available commercially from Beckman Coulter, Inc. under the trademark "iTopia™" Epitope Discovery System.

After finding a parent peptide having suitable binding characteristics, the present invention requires at least one suitable modification to the peptide so as to preferably increase immunogenicity. That modification involves replacing at least one primary anchor residue for the particular MHC of interest with an appropriate non-natural amino acid. In one embodiment, for HLA A2 epitopes, the primary anchor residue that is substituted is at the P2 position in a 9-mer or a 10-mer. In another embodiment, there are two substitutions, where the first substitution is at P2 and the second substitution is at the terminal residue position (i.e., PΩ). For example, for a 9-mer, there is a substitution at both P2 and P9; and for a 10-mer, there is a substitution at both P2 and P10.

Once a peptide has been modified by appropriate substitution, it can be tested to determine if it is a peptide derivative of the present invention. As described above, a peptide derivative of the present invention triggers an expansion of T cells that recognize the parent peptide. Preferably, the peptide derivative is also more immunogenic than its parent peptide and preferably will exhibit at least one, at least two, at least three, at least four, or all five of the following properties compared to the corresponding parent peptide: (a) it generates a T-cell immune response that is greater than the T-cell immune response generated by the parent peptide; (b) it binds to MHCI with an affinity that is higher than the affinity with which the parent peptide binds to MHCI, i.e., the peptide derivative has a lower $K_D$ than the parent peptide; (c) the affinity of T-cell receptors for the complex formed between MHCI and a peptide derivative of the present invention is higher than the affinity of T-cell receptors for the complex formed between MHCI and the parent peptide; (d) a complex formed between MHCI and a peptide derivative of the present invention is more stable (i.e., has a slower off-rate) than a complex formed between MHCI and the parent peptide; and (e) the peptide derivative of the present invention triggers an expansion of a broader number of T-cell clones that recognize the parent peptide than are triggered by the parent peptide.

4.3. Synthesis of Peptide Derivatives

Peptide derivatives of the present invention can be prepared by any suitable method, e.g., by solid phase synthesis. The coupling of amino acids and amino acid analogs can be accomplished by techniques familiar to those in the art and described, e.g., in Stewart and Young, 1984, "Solid Phase Synthesis", Second Edition, Pierce Chemical Co., Rockford, Ill. Amino acids and amino acid analogs used for peptide synthesis can be standard Boc ($N^\alpha$-amino-protected $N^\alpha$-t-butyloxycarbonyl) amino acid or amino acid analog resin with standard deprotecting, neutralization, coupling and wash protocols of the original solid phase procedure of Merrifield (1963, J. Am. Chem. Soc. 85:2149-2154), or the base-labile $N^\alpha$-amino protected 9-fluorenylmethoxycarbonyl (Fmoc) amino acids first described in Carpino and Han (1972, J. Org. Chem. 37:3403-3409). Both Fmoc and Boc α-amino protected amino acids and amino acid analogs can be obtained from Fluka, Bachem, Advanced Chemtech, Sigma, Cambridge Research Biochemical, Peninsula Labs, or other chemical companies familiar to those who practice in this field. In addition, the invention can be practiced with other $N^\alpha$-protecting groups familiar to those of skill in the art.

Many methods of activation can be used in the practice of the present invention and include, e.g., the use of preformed symmetrical anhydride (PSA), preformed mixed anhydride (PMA), acid chlorides, active esters, and in situ activation of the carboxylic acid, as described by Fields and Noble (1990, Int. J. Pept. Protein Res. 35:161-214).

Solid phase peptide synthesis can be accomplished by techniques familiar to those in the art in view of the present disclosure, and described, e.g., in Stewart and Young, supra, as well as in Fields and Noble, supra, or by using automated synthesizers such as sold by ABS.

The completeness of coupling should be assessed. Those skilled in the art will be familiar with well known quantitative monitoring tests such as ninhydrin (the Kaiser test), picric acid, 2,4,6-trinitro-benzenesulfonic (TNBS), fluorescamine, and chloranil, which are based on reagent reaction with free amino groups to produce a chromophoric compound. If imino acids (e.g., Pro and Hyp) are used, isatin monitoring is a preferred method (Fields and Noble, supra). Quantification of reaction completeness can be monitored during the course of the reaction as described, e.g., by Salisbury et al. (International PCT Publication WO 91/03485). If the coupling reaction is incomplete as determined by this test, the reaction can be forced to completion by several methods familiar to those in the art, including: (a) a second coupling using a one- to five-fold excess of protected amino acid or amino acid analog; (b) an additional coupling using different or additional solvents (e.g., trifluoroethane); or (c) the addition of chaotropic salts, e.g., $NaClO_4$ or LiBr (Klis an Stewart, "Peptides: Chemistry, Structure and Biology"; in Rivier and Marshall (eds) ESCOM Publ. 1990, pp. 904-906).

Once synthesized, a peptide derivative of the present invention can be covalently or non-covalently complexed to a macromolecular carrier, including, but not limited to, natural and synthetic polymers, proteins, polysaccharides, poly(amino acid), polyvinyl alcohol, polyvinyl pyrrolidone, and lipids. A peptide derivative of the present invention can be conjugated to a fatty acid for introduction into a liposome. U.S. Pat. No. 5,837,249. A peptide derivative of the present invention can be covalently or non-covalently complexed to a solid support. A peptide derivative of the present invention can be covalently bound to one or more molecules of polyethylene glycol (PEG). A peptide derivative of the present invention can be associated with an antigen-presenting matrix with or without co-stimulatory molecules, as known in the art.

4.4. Therapeutic Methods

The peptide derivative of the present invention may be administered as part of a longer peptide or polypeptide and/or it may be fused to a moiety to increase its half life in vivo. The peptide derivative, polypeptide or fusion comprising said derivative, may be administered as part of a pharmaceutically acceptable composition. The present invention provides a method of inducing an immune response by administering a peptide derivative of the invention to a subject, or by contacting a cell(s) with the peptide derivative. The peptide derivative induces an immune response, e.g., against the corresponding parent peptide, target antigen, tumor or cancer cell, or infectious agent.

In a preferred embodiment, the present invention provides a method of treating or preventing a cancer. The method includes administering to a subject in need of such treatment a therapeutically effective amount of an appropriate peptide derivative of the present invention. Effective treatment may require administration of multiple doses to maximize the therapeutic effect.

Cancers, including any disease, disorder or symptom characterized by uncontrolled cell growth, in which cancer cells express a cancer-associated antigen as described herein having immunogenic properties relevant to human cancers, can be treated by administering to a subject in need of said treatment or prevention an appropriate peptide derivative of the present invention. Whether a particular therapeutic agent is effective in treating or preventing a certain type of cancer can be determined by any method known in the art.

Peptide derivatives of the present invention are useful as therapeutic agents to treat or prevent a cancer selected from, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, colon carcinoma, pancreatic cancer, breast cancer, ovarian cancer, prostate cancer, lymphoma, leukemia, squamous cell carcinoma, basal cell carcinoma, adenocarcinoma, hepatocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In a preferred embodiment, peptide derivatives of the present invention are useful as agents to treat or prevent melanoma. In said embodiment, the peptide derivatives are preferably MART-1-based peptide derivatives.

In a further preferred embodiment, peptide derivatives of the present invention are useful as agents to treat or prevent Survivin-expressing cancer. In said embodiment, the peptide derivatives are preferably based on a peptide selected from the Survivin protein, in particular they are selected from the group consisting of the Survivin-based peptide derivatives of the present invention.

In certain embodiments of the present invention, the subject being treated with the peptide derivative of the present invention is also treated with one or more other therapeutic cancer treatments selected from surgery, radiation therapy, immunotherapy, and chemotherapy. In particular, the therapeutic agent of the present invention used to treat or prevent cancer can be administered in conjunction with one or more chemotherapeutic agents, such as, e.g., methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, docetaxel, among others. The peptide derivative and the other therapeutic treatment can be provided to a subject in any manner and following any regimen that provides a benefit of combination therapy. Thus, the two treatments can be given simultaneously, or sequentially. The durations of treatment with the two therapies may be the same or different.

Peptide derivatives of the present invention are also useful as therapeutic agents to treat or prevent infection including, but not limited to, parasitic infections (such as those caused by plasmodial species, among others), viral infections (such as those caused by influenza viruses, leukemia viruses, immunodeficiency viruses such as HIV, papilloma viruses, herpes virus, hepatitis viruses, measles virus, poxviruses, mumps virus, cytomegalovirus, Epstein-Barr virus, among others), bacterial infections involving MHCI (such as those caused by *staphylococcus, streptococcus, pneumococcus, Neisseria gonorrhea, Borrelia, pseudomonas, mycobacteria, Salmonella*, among others), or against any infectious agent that enters cells as part of its lifecycle. In certain embodiments of the present invention, the subject being treated with the peptide derivative of the present invention is also treated with one or more antibiotics or antivirals.

4.5. Pharmaceutical Formulations and Administration

The present invention further provides a pharmaceutical formulation containing a peptide derivative of the present invention combined with a pharmaceutically acceptable carrier. In one embodiment, the pharmaceutical composition comprises a therapeutically effective amount of a peptide derivative of the present invention. Such formulations can be varied depending upon the intended use and route of administration.

Many routes of administration can be selected to administer a pharmaceutical composition of the present invention, including but not limited to the oral, intracerebral, intradermal, intramuscular, intraperitoneal, intravenous, intra-arterial, subcutaneous, intranasal, vaginal, rectal, buccal, sublingual, transdermal, and mucosal, and scarification (i.e., scratching through the top layers of skin; see, e.g., Glenn et al., 1998, Nature 391:851; Glenn et al., 1998, J. Immunol. 161:3211-3214) routes, or by any other route of administration determined to be appropriate under the circumstances of each case.

A suitable pharmaceutical composition can be formulated as an injectable, either as a liquid solution or suspension. A solid form suitable for solution or suspension in a liquid prior to injection may also be prepared. The formulation can also be emulsified. The therapeutic agent is often mixed with excipients that are pharmaceutically acceptable and compatible with the active ingredient. Suitable excipients include water, saline, buffered saline, dextrose, glycerol, ethanol, sterile isotonic aqueous buffer and the like, and combinations thereof. In addition, the formulation may include minor amounts of auxiliary substances such as wetting or emulsifying agents, pH buffering agents, and/or adjuvants that enhance the effectiveness of the vaccine. A peptide derivative of the invention can be introduced to a subject in microspheres or microcapsules, e.g., prepared from PLGA (see U.S. Pat. Nos. 5,814,344; 5,100,669; and 4,849,222; PCT Publication Nos. WO 95/11010 and WO 93/07861; Johansen et al., 2000, Vaccine 18: 209-215). Alternatively, a peptide derivative of the invention can be encapsulated in liposomes (Ludewig et al., 2001, Vaccine 19:23-32; Copland et al., 2003, Vaccine 21: 883-890; Chang et al., 2001, Vaccine 19:3608-3614). Alternatively, a peptide derivative of the invention can be encapsulated in ISCOMs (Morein et al., 1984, Nature 308:457-460; Lenarczyk et al., 2004, Vaccine 22: 963-974). Alternatively, a peptide derivative of the invention can be encapsulated in virus like particles (VLPs) (Storni et al., 2004, J. Immunol. 172:1777-1785). Other technologies are available to enable alternative formulations.

The pharmaceutical composition of the present invention can be a liquid solution, a suspension, an emulsion, a tablet, a pill, a capsule, a sustained release formulation, a suppository, or a powder. For oral administration, the formulation can be, e.g., a tablet or capsule prepared by conventional means using pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and wetting agents (e.g., sodium lauryl sulphate). The tablets can be coated by methods known in the art. Liquid preparations for oral administration can take the form, e.g., of solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), and preservatives (e.g., methyl or propyl-p-hydroxybenzoates or sorbic acid). The preparations can also contain buffer salts, flavoring, coloring and sweetening agents as appropriate.

Suitable pharmaceutical excipients are described in "Remington's Pharmaceutical Sciences" by E. W. Martin, 18$^{th}$ Edition.

The components of the pharmaceutical composition can be supplied either separately or mixed together in a unit dosage form, e.g., as a dry lyophilized powder or water-free concentrate in a sealed container such as a vial or sachette indicating the quantity of therapeutically active agent. Where the composition is administered by injection, an ampoule of sterile diluent can be provided so that the ingredients can be mixed prior to administration.

In a specific embodiment, lyophilized peptide derivative of the present invention is provided in a first container, and a second container comprises a diluent, preferably a diluent consisting of an aqueous solution of 50% glycerin, 0.25% phenol, and an antiseptic (e.g., 0.005% brilliant green).

The pharmaceutical composition may further comprise an adjuvant component to assist in potentiating the response to the peptide derivative. The term "adjuvant" refers to a compound or mixture that may be non-immunogenic when administered to a subject alone, but that augments the subject's immune response to another antigen when administered conjointly with that antigen. The adjuvant can be administered as part of a pharmaceutical composition of the present invention, or as a separate formulation. Adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-gamma, IL-2, IL-12 or GM-CSF; synthetic adjuvants such as nonionic block copolymers, muramyl peptide analogues (e.g., N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy]-ethylamine), polyphosphazenes, or synthetic polynucleotides, and surface active substances such as lysolecithin, pluronic polyols, polyanions, peptides, hydrocarbon emulsions, keyhole limpet hemocyanins (KLH), or imiquimod (Testerman et al., 1995, J. Leukocyte Biol. 58:537-545). Preferably, these adjuvants are pharmaceutically acceptable for use in humans.

Administration of a pharmaceutical composition of the present invention to a subject is intended to treat or prevent a disease, disorder or symptom by triggering the development of protective immunity in the subject. Within the meaning of the present invention, protective immunity may be partial or complete. In a specific embodiment of the present invention, protective immunity can be reflected by any improvement in any condition or symptom being treated, including any one of the following: a slowing of disease progression, increasing length to relapse, decreased rate of tumor growth, tumor regression, decreased mortality, etc.

The present invention further provides a pharmaceutical kit comprising a container comprising a therapeutically effective amount of a peptide derivative of the present invention. The kit may further comprise a second container comprising a sterile diluent that can be used to reconstitute or dilute the peptide derivative in the first container to the appropriate concentration for administration. The kit may further comprise a printed notice in a form prescribed by a governmental agency regulating the manufacture, use or sale of pharmaceuticals or biological products which notice describes the use of the peptide derivative to treat or prevent a disease or disorder, and reflects approval by the agency of the manufacture, use or sale of the peptide derivative for human administration. The kit preferably contains one or more unit dosage forms of the therapeutic agent. The kit may comprise metal or plastic foil, such as a blister pack.

According to the therapeutic methods of the present invention, the pharmaceutical compositions described herein can be administered to a subject at therapeutically effective or immunogenically effective dose, and preferably, with minimal toxicity.

Following methodologies which are well-established in the art (see, e.g., reports on evaluation of several vaccine formulations in a collaborative effort between the Center for Biological Evaluation and Food and Drug Administration and the National Institute of Allergy and Infectious Diseases (Goldenthal et al., National Cooperative Vaccine Development Working Group, AIDS Res. Hum. Retroviruses, 1993, 9:545-549)), effective doses and toxicity of compounds and compositions of the instant invention can first be determined in preclinical studies using small animal models (e.g., mice) in which these compounds and compositions have been found to be immunogenic and that can be reproducibly immunized by the same route proposed for the human clinical trials. Preferably, mice that are transgenic for the relevant human MHCI molecule are used.

In a specific embodiment, the efficiency of epitope-specific CD8+ T-cell responses to the pharmaceutical and vaccine compositions of the present invention is determined by the enzyme-linked immunospot technique (ELISPOT). ELISPOT is a standard method in the art (Miyahira et al., 1995, J. Immunol. Meth., 181: 45-54; Guelly et al., 2002, Eur. J. Immunol., 32:182-192; Nikitina and Gabrilovich, 2001, Int. J. Cancer, 94:825-833; Field et al., 2001, Immunol. Rev., 182:99-112; Altfeld et al., 2001, J. Immunol., 167:2743-2752; Skoberne et al., 2001, J. Immunol., 167: 2209-2218). This method employs pairs of antibodies directed against distinct epitopes of a cytokine, and allows the visualization of cytokine secretion by individual T-cells following in vitro stimulation with an antigen. ELISPOT has the advantage of detecting only activated/memory T-cells, and the cytokine release can be detected at single cell levels, allowing direct determination of T-cell frequencies (Czerkinsky et al., 1988, J. Immunol. Methods, 25:29; Taguchi et al., 1990, J. Immunol. Methods, 128:65). The cytokine captured by the immobilized antibody in the ELISPOT assay can be detected in situ using an insoluble peroxidase substrate. Thus, the cytokine secretion by individual cells can be clearly visualized. The high sensitivity and easy performance, allowing a direct enumeration of peptide-reactive T-cells without prior in vitro expansion, make the ELISPOT assay well suited to monitor and measure T-cell responses, particularly CD8+ T-cell responses of very low frequencies. According to alternative embodiments, the efficiency of an epitope-specific CD8+ T-cell response to a peptide derivative or pharmaceutical composition of the present invention can be determined using other art-recognized immunodetection methods such as, e.g., ELISA (Tanguay and Killion, 1994, Lymphokine Cytokine Res. 13:259) and intracellular staining (Carter, L. L. and Swain, S. L. 1997, Curr. Opin. Immunol. 9, 177-182).

For any peptide derivative or pharmaceutical composition used in a therapeutic method of the present invention, the therapeutically effective dose can be estimated initially from animal models and based on knowledge in the art to achieve a dose that induces an immune response. In safety determinations for each composition, the dose and frequency of immunization should preferably meet or exceed those anticipated for use in the clinical trial.

The choice and amount of peptide derivative, and the selection and amount of other components in the pharmaceutical composition, depend on the disease, disorder or symptom being treated, as well as on the route of administration. Determination of the proper dose and treatment regimen will typically vary depending on the circumstances and conditions of the particular subject being treated, including age, body weight, gender, general health conditions, sensitivity, current administration of other drugs, and stage or seriousness of the disease, disorder or symptom being treated. The appropriate dose and dosage times should preferably be decided according to the judgment of a medical practitioner and each subject's circumstances according to standard clinical techniques and in view of published clinical reports. The appropriate pharmaceutical composition can be administered continuously or intermittently depending on a subject's response to treatment, and either alone or in combination with one or more other therapeutic agents to treat the same or a different disease, disorder, condition or symptom. Effective doses may be extrapolated from dose-response curves derived from animal model test systems, including transgenic animal models.

The following examples further describe the materials and methods used in carrying out the invention. The examples are not meant to limit the invention in any manner.

5. EXAMPLES

5.1. Affinity and Stability of HLA-A201/Peptide Complexes

Modified peptides were tested for their ability to bind to and stabilize the HLA-A0201 molecule using one of two assays: (i) a live cell/flow cytometry-based assay; or (ii) a soluble class I/plate based-assay. E.g., Sharma et al., J. Biol. Chem. 276:21443-49 (2001); Pogue et al., PNAS 92:8166-70 (1995).

I. Live Cell/Flow Cytometry-Based Assays
  Relative Binding Affinity.

The live cell/flow cytometry-based assay is a well-established assay utilizing the TAP-deficient hybridoma cell line T2 (American Type Culture Collection (ATCC Accession No. CRL-1992), Manassas, Va.). The TAP deficiency in this cell line leads to inefficient loading of MHCI in the ER and an excess of empty MHCIs. Salter and Cresswell, EMBO J. 5:943-49 (1986); Salter, Immunogenetics 21:235-46 (1985). Empty MHCIs are highly unstable, and are therefore short-lived. When T2 cells are cultured at reduced temperatures, empty MHCIs appear transiently on the cell surface, where they can be stabilized by the exogenous addition of MHCI-binding peptides. To perform this binding assay, peptide-receptive MHCIs were induced by culturing aliquots of $10^7$ T2 cells overnight at 26° C. in serum free AIM-V medium alone, or in medium containing escalating concentrations (0.1 to 100 uM) of peptide. Cells were then washed twice with PBS, and subsequently incubated with a fluorescent tagged HLA-A0201-specific monoclonal antibody, BB7.2, to quantify cell surface expression. Samples were acquired on a FACS Calibur instrument (Becton Dickinson) and the mean fluorescence intensity (MFI) determined using the accompanying Cellquest software.

The specific increase in mean fluorescent intensity (MFI) was used as a measure of peptide binding, and was calculated as follows:

$$\frac{MFI \text{ with modified peptide}}{MFI \text{ without peptide}} \times 100$$

The relative efficiency with which a peptide stabilizes an MHCI at the surface of these cells is used as a measure of relative binding affinity. To determine the relative binding affinity, maximal binding was determined using the influenza matrix$_{58-66}$ peptide as a control, which peptide has been shown to bind to HLA-A0201 with high affinity. The relative binding affinity for each test peptide was taken as the concentration of the test peptide at which 50% maximal binding occurs.

Assessment of Peptide/HLA-A0201 Complex Stability.

Aliquots of $10^7$ T2 cells were cultured overnight at 26° C. in serum-free AIM-V medium alone, or in medium containing peptide at a concentration of 100 uM. Cells were then incubated with Brefeldin A at 10 ug/ml for 1 hour, washed, and subsequently incubated at 37° C. for 0, 2, 4 or 6 hours in the presence of 0.5 ug/ml Brefeldin A. Cells were washed and stained with fluorescently tagged BB7.2 to quantify cell surface expression of HLA-A0201. The time required for the loss of 50% of the complexes stabilized at time 0 ($DC_{50}$) was used as a measure of the stability of the peptide/HLA-A0201 complex.

II. Soluble Class I/Plate-Based Assays
  Relative Binding Affinity.

The plate-based assay, named iTopia™, is a commercial assay (Beckman Coulter). The assay is performed in wells of microtiter plates. At the outset of the assay, MHCI complexes (properly folded MHC heavy chain, beta 2 microglobulin and a place-holder peptide), are tethered to streptavidin-coated microplate wells. (Proper formation/folding of the MHC complex may be determined by binding of an anti-HLA-ABC antibody.) A buffer designed to unfold and dissociate the complex was added to each test well, allowed to incubate, and the place holder peptide and beta 2 microglobulin were washed away. Escalating concentrations of the test peptide, along with additional beta 2 microglobulin, were added to each well and incubated in a buffer designed to promote refolding of complexes. Plates were incubated overnight at 21° C. Properly folded MHCI complex molecules were detected with a fluorescently labeled antibody selected based on its ability to only bind properly folded MHCI complexes. Binding was reported relative to a standardized positive control peptide. Relative affinities were reported as $ED_{50}$, and are defined herein as the concentration of peptide required to achieve half maximal binding of the positive control. The lower the $ED_{50}$ value, the stronger the binding of the peptide to MHCI.

Assessment of Peptide/HLA-A0201 Complex Stability.

MHCI complexes were dissociated in each test well using stripping buffer, and the place-holder peptide and beta 2 microglobulin were washed away. 100 uM of the test peptide was added to appropriate wells along with additional beta 2 microglobulin and the anti-HLA ABC antibody, and the plates were incubated overnight at 21° C. Plates were washed, and fresh buffer was added to each well. Plates were shifted to 37° C., and the appropriate wells were read at 0, 0.5, 1, 1.5, 2, 4, 6 and 8 hours. The half-life of the complex was used as a measure of its stability, and is calculated as the amount of time required for loss of 50% of the complexes formed at time 0.

5.2. Immunogenicity of Peptides

Generation of Peptide Specific T-Cells.

In vitro education (IVE) assays were used to test the ability of each test peptide to expand CD8+ T-cells. Mature professional APCs were prepared for these assays in the following way. 80-90×10⁶ PBMCs isolated from a healthy human donor were plated in 20 ml of RPMI media containing 2% human AB serum, and incubated at 37° C. for 2 hours to allow for plastic adherence by monocytes. Non-adherent cells were removed and the adherent cells were cultured in RPMI, 2% human AB serum, 800 IU/ml of GM-CSF and 500 IU/ml of IL-4. After 6 days, TNF-alpha was added to a final concentration of 10 ng/ml. On day 7, the dendritic cells (DC) were matured either by the addition of 12.5 ug/ml poly I:C or 0.3 ug/ml of CD40L. The mature dendritic cells (mDC) were harvested on day 8, washed, and either used directly or cryopreserved for future use.

For the IVE of CD8+ T-cells, aliquots of 2×10⁵ mDCs were pulsed with each peptide at a final concentration of 100 uM, incubated for 4 hours at 37° C., and then irradiated (2500 rads). The peptide-pulsed mDCs were washed twice in RPMI containing 2% human AB serum. 2×10⁵ mDCs and 2×10⁶ autologous CD8+ cells were plated per well of a 24-well plate in 2 ml of RPMI containing 2% human AB, 20 ng/ml IL-7 and 100 pg/ml of IL-12, and incubated for 12 days. The CD8+ T-cells were then re-stimulated with peptide-pulsed, irradiated mDCs. Two to three days later, 20 IU/ml IL-2 and 20 ng/IL7 were added. Expanding CD8+ T-cells were re-stimulated every 8-10 days, and were maintained in media containing IL-2 and IL-7. Cultures were monitored for peptide-specific T-cells using a combination of functional assays and/or tetramer staining. Parallel IVEs with the modified and parent peptides allowed for comparisons of the relative efficiency with which the peptides expanded peptide-specific T-cells.

5.3. Quantitative and Functional Assessment of CD8+ T-Cells

Tetramer Staining.

MHC tetramers were purchased from Beckman Coulter (San Diego, Calif.), and were used to measure peptide-specific T-cell expansion in the IVE assays. For the assessment, tetramer was added to 1×10⁵ cells in PBS containing 1% FCS and 0.1% sodium azide (FACS buffer) according to manufacturer's instructions. Cells were incubated in the dark for 20 min at room temperature. Antibodies specific for T-cell markers, such as CD8, were then added to a final concentration suggested by the manufacturer, and the cells were incubated in the dark at 4° C. for 20 min. Cells were washed with cold FACS buffer and resuspended in buffer containing 1% formaldehyde. Cells were acquired on a FACS Calibur (Becton Dickinson) instrument, and were analyzed by use of Cellquest software (Becton Dickinson). For analysis of tetramer positive cells, the lymphocyte gate was taken from the forward and side-scatter plots. Data were reported as the percentage of cells that were CD8+/Tetramer−.

ELISPOT.

Peptide-specific T-cells were functionally enumerated using the ELISPOT assay (BD Biosciences), which measures the release of IFNgamma from T-cells on a single cell basis. Target cells (T2 or HLA-A0201 transfected C1Rs) were pulsed with 10 uM peptide for 1 hour at 37° C., and washed three times. 1×10⁵ peptide-pulsed targets were co-cultured in the ELISPOT plate wells with varying concentrations of T-cells (5×10² to 2×10³) taken from the IVE culture. Plates were developed according to the manufacturer's protocol, and analyzed on an ELISPOT reader (Cellular Technology Ltd.) with accompanying software. Spots corresponding to the number of IFNgamma-producing T-cells were reported as the absolute number of spots per number of T-cells plated. T-cells expanded on modified peptides were tested not only for their ability to recognize targets pulsed with the modified peptide, but also for their ability to recognize targets pulsed with the parent peptide.

CD107 Staining.

CD107a and b are expressed on the cell surface of CD8+ T-cells following activation with cognate peptide. The lytic granules of T-cells have a lipid bilayer that contains lysosomal-associated membrane glycoproteins ("LAMPs"), which include the molecules CD107a and b. When cytotoxic T-cells are activated through the T-cell receptor, the membranes of these lytic granules mobilize and fuse with the plasma membrane of the T-cell. The granule contents are released, and this leads to the death of the target cell. As the granule membrane fuses with the plasma membrane, C107a and b are exposed on the cell surface, and therefore are markers of degranulation. Because degranulation as measured by CD107 a and b staining is reported on a single cell basis, the assay is used to functionally enumerate peptide-specific T-cells. To perform the assay, peptide was added to HLA-A0201-transfected cells C1R to a final concentration of 20 uM, the cells were incubated for 1 hour at 37° C., and washed three times. 1×10⁵ of the peptide-pulsed C1R cells were aliquoted into tubes, and antibodies specific for CD107 a and b were added to a final concentration suggested by the manufacturer (Becton Dickinson). Antibodies are added prior to the addition of T-cells in order to "capture" the CD107 molecules as they transiently appear on the surface during the course of the assay. 1×10⁵ T-cells from the IVE culture were added next, and the samples were incubated for 4 hours at 37° C. The T-cells were further stained for additional cell surface molecules such as CD8 and acquired on a FACS Calibur instrument (Becton Dickinson). Data was analyzed using the accompanying Cellquest software, and results were reported as the percentage of CD8+ CD107 a and b+ cells.

CTL Lysis.

Cytotoxic activity was measured using a chromium release assay. Target T2 cells were labeled for 1 hour at 37° C. with Na⁵¹Cr and washed. 5×10³ target T2 cells were then added to varying numbers of T-cells from the IVE culture. Chromium release was measured in supernatant harvested after 4 hours of incubation at 37° C. The percentage of specific lysis was calculated as:

$$\frac{\text{Experimental release} - \text{spontaneous release}}{\text{Total release} - \text{spontaneous release}} \times 100$$

5.4. Results

Table 2. Using the iTopia™ plate-based assay system from Beckman Coulter, the stability of complexes formed between the MART-1 peptide derivatives and HLA-A2 were determined. Several of the peptide derivatives formed complexes with HLA-A2 that were significantly more stable than those formed with the native MART-1 peptide (SEQ ID NO: 1). Derivative peptides with SEQ ID NOs: 7 and 16 formed complexes with HLA-A2 that had half-lives greater than 100 hours.

Table 3. An ELISPOT assay measuring IFNgamma production (a marker of CD8+ T-cell activation) was used to determine if CD8+ T-cells expanded in the presence of dendritic cells pulsed with the MART-1 peptide derivatives would recognize target cells pulsed with the native MART-1 peptide. For three of the four peptide derivatives tested (SEQ ID NOs: 15, 16 and 18), the expanded T-cells recognized equally well target cells pulsed with either the native MART-1 peptide or the peptide derivatives as indicated by the similarly high levels of IFNgamma produced.

Table 4. CD107 a and b are markers of CD8+ T-cell activation and degranulation. Analyzing CD107 expression using a FACS Calibur instrument, CD8+ T-cells expanded in the presence of dendritic cells pulsed with the MART-1 peptide derivatives were tested for their ability to recognize target cells pulsed with the native MART-1 peptide. All four of the CD8+ T-cell populations expanded with the derivative peptides, recognized target cells pulsed with the native MART-1 peptide as shown by the increased levels of CD107 expression detected.

Table 5. The stability of complexes formed using HLA-A2 with native survivin peptides and survivin peptide derivatives was tested using the iTopia™ plate-based assay system from Beckman Coulter. For both examples tested, the peptide derivative was found to form a more stable complex with HLA-A2 than the corresponding native peptide (compare SEQ ID NO: 21 to 26 and SEQ ID NO: 31 to 36). Notably, the survivin peptide derivative (SEQ ID NO: 36) showed a greater than 20-fold increase in the half life of the HLA-A2 peptide complex when compared to the native survivin peptide.

TABLE 2

Stability of HLA-A2/MART-1 Peptide Derivative Complex

| Peptide Used In Binding Assay | SEQ ID NO: | Half Life of Complex (hr) |
|---|---|---|
| AAGIGILTV[1] | 1 | 1.4 |
| A-[cpg]-GIGILTV | 7 | >100 |
| E-[c3a]-AGIGILTV | 13 | 23.6 |
| E-[chg]-AGIGILTV | 15 | 31.0 |
| E-[cpg]-AGIGILTV | 16 | >100 |
| E-[dfb]-AGIGILTV | 17 | 13.9 |
| E-[dhl]-AGIGILTV | 18 | 5.5 |
| E-[phg]-AGIGILTV | 19 | 6.5 |
| E-[sta]-AGIGILTV | 20 | 15.3 |
| E-[c5g]-AGIG-[amv]-LTV | 49 | 11.9 |

[1]Native MART-1 nonamer peptide

TABLE 3

T-Cells Expanded on MART-1 Peptide Derivative Recognize Targets Pulsed with the Native MART-1 Peptide

| Peptide Used to Generate T-Cells | SEQ ID NO: | IFNγ Production for Targets Pulsed with Native MART-1 | IFNγ Production for Targets Pulsed with MART-1 Peptide Derivative |
|---|---|---|---|
| AAGIGILTV | 1 | 11 | |
| E-[chg]-AGIGILTV | 15 | 279 | 261 |
| E-[cpg]-AGIGILTV | 16 | 182 | 273 |
| E-[dhl]-AGIGILTV | 18 | 336 | 239 |
| E-[phg]-AGIGILTV | 19 | 35 | 30 |

TABLE 4

T-Cells Expanded on MART-1 Peptide Derivatives Recognize Targets Pulsed with the Native MART-1 Peptide

| Peptide Used to Generate T-Cells | Sequence ID No. | %CD8+ T-cells Degranulating (CD107+) for Targets Pulsed with Native MART-1 | %CD8+ T-cells Degranulating (CD107+) for Targets Pulsed with MART-1 Peptide Derivative |
|---|---|---|---|
| AAGIGILTV | 1 | 4 | |
| E-[chg]-AGIGILTV | 15 | 56 | 61 |
| E-[cpg]-AGIGILTV | 16 | 37 | 60 |

TABLE 4-continued

T-Cells Expanded on MART-1 Peptide Derivatives
Recognize Targets Pulsed with the Native MART-1 Peptide

| Peptide Used to Generate T-Cells | Sequence ID No. | %CD8+ T-cells Degranulating (CD107+) for Targets Pulsed with Native MART-1 | %CD8+ T-cells Degranulating (CD107+) for Targets Pulsed with MART-1 Peptide Derivative |
|---|---|---|---|
| E-[phg]-AGIGILTV | 19 | 11 | 20 |
| E-[sta]-AGIGILTV | 20 | 32 | 37 |

TABLE 5

Stability of Survivin Peptide/HLA-A2 Complexes

| Peptide Used in Binding Assay | Sequence ID. No. | Half Life of Complex (hr) |
|---|---|---|
| ISTFKNWPF[2] | 21 | 0.24 |
| I-[cpg]-TFKNWPF | 26 | 1.9 |
| KVRRAIEQL[3] | 31 | 1.9 |
| K-[cpg]-RRAIEQL | 36 | 50.6 |

[2] Native Survivin 19-27
[3] Native Survivin 130-138

While the invention has been described and illustrated with reference to certain preferred embodiments thereof, those skilled in the art will appreciate that obvious modifications can be made herein without departing from the spirit and scope of the invention. Such variations are contemplated to be within the scope of the appended claims.

All references cited herein are hereby incorporated by reference in their entireties.

TABLE 6

HLA Class I Alleles

| Sero-type | Geno-type | Total No. Alleles | NCBI Entry | Reference |
|---|---|---|---|---|
| A02 | 20101 | 89 | AJ555412 | Koller et al., J Immunology 134: 2727-2733, 1988 |
| A01 | 10101 | 11 | AJ278305 | Girdlestone, Nucleic Acid Research 18: 6701-6701, 1990 |
| A03 | 10101 | 18 | X00492 | Strachan et al., EMBO J 3: 887-894, 1984 |
| A11 | 101 | 20 | X12781 | Cowan et al., Immunogenetics 25: 241-250, 1987 |
| A24 | 20101 | 50 | L47206 | Magor et al., J Immunology 158: 5242-5250, 1997 |
| A68 | 101 | 30 | AJ315642 | Holmes et al., EMBO J 4: 2849-2854, 1985 |
| B07 | 201 | 40 | M32317 | Takiguchi et al., J Immunology 143: 1372-1378, 1989 |
| B08 | 1 | 22 | M24036 | Parham et al., PNAS USA 85: 4005-4009, 1988 |
| B15 | 10101 | 98 | U03859 | Hildebrand et al., Tissue Antigens 43: 209-218, 1994 |
| B27 | 2 | 30 | L38504 | Seemann et al., EMBO J 5: 547-552, 1986 |
| B35 | 101 | 56 | M28115 | Ooba et al., Immunogenetics 30: 76-80, 1989 |
| B40 | 101 | 63 | U03698 | Ways et al., Immunogenetics 25: 323-328 1987 |
| B44 | 20101 | 43 | M24038 | Parham et al., PNAS USA 85: 4005-4009, 1988 |
| B51 | 101 | 41 | M28205 | Pohla et al., Immunogenetics 29: 297-307, 1989 |
| Cw03 | 23 | 23 | M84172 | Zemmour et al., Tissue Antigens 39: 249-257, 1992 |
| Cw04 | 17 | 17 | M26432 | Ellis et al., J Immunology 142: 3281-3285, 1989 |
| Cw05 | 11 | 11 | AJ010748 | Baurain et al., Tissue Antigens 53: 510-512, 1999 |
| Cw06 | 11 | 11 | M28160 | Mizuno et al., Immunogenetics 29: 323-330, 1989 |
| Cw07 | 34 | 34 | D38526 | Wang et al., Human Immunology 45: 52-58, 1996 |
| Cw12 | 19 | 19 | M28172 | Takiguchi et al., J Immunology 143: 1372-1378, 1989 |

TABLE 7

HLA Binding Motifs

| Genotype | Motif | Reference |
|---|---|---|
| A*01 | xx[DE]xxxxx[Y] | SYFPEITHI |
| A*0101 | xx[DE]xxxxx[Y] | Marsh2000 |
| A*0201 | x[L(M)]xxxxxx[V(L)] | Marsh2000 |
| A*0201 | x[LM]xxxxxx[VL] | SYFPEITHI |
| A*0202 | x[L]xxxxxx[L] | Marsh2000 |
| A*0202 | x[L(A)]xxxxxx[LV] | SYFPEITHI |
| A*0204 | x[L]xxxxxx[L] | Marsh2000 |
| A*0204 | x[L]xxxxxx[L] | SYFPEITHI |
| A*0205 | x[V(QL)]xxxxxx[L] | Marsh2000 |
| A*0205 | xxxxxxxx[L] | SYFPEITHI |
| A*0206 | x[V(Q)]xxxxxx | Marsh2000 |
| A*0206 | x[V(Q)]xxxxxx[V(L)] | SYFPEITHI |

TABLE 7-continued

HLA Binding Motifs

| Genotype | Motif | Reference |
|---|---|---|
| A*0207 | x[L][D]xxxxx[L] | Marsh2000 |
| A*0207 | x[L]xxxxxx[L] | SYFPEITHI |
| A*0214 | x[QV]xxx[K]xx[VL] | Luscher2001 |
| A*0214 | x[VQ(L)]xxxxxx[L] | Marsh2000 |
| A*0214 | x[VQL(A)]xxxxxx[L(VM)] | SYFPEITHI |
| A*0217 | x[L]xxxxxx[L] | SYFPEITHI |
| A*03 | x[LVM]xxxxxx[KYF] | SYFPEITHI |
| A*0301 | x[LVM(IAST)]xxxxxx[KY(FR)] | Marsh2000 |
| A*1101 | xxxxxxxx[K] | Marsh2000 |
| A*1101 | xxxxxxxx[KR] | SYFPEITHI |
| A*24 | x[Y(F)]xxxxxx[ILF] | SYFPEITHI |
| A*2402 | x[YF]xxxxxx[FWIL] | Marsh2000 |
| A*2402 | x[YF]xxxxxx[LFI] | SYFPEITHI |
| A*2501 | xxxxxxxxx[W] | Yusim2004 |
| A*2601 | x[VTIFL]xxxxxx[YF] | Marsh2000 |
| A*2601 | x[VTILF]xxxxxx[YF] | SYFPEITHI |
| A*2602 | x[VTILF]xxxxxx[YFML] | Marsh2000 |
| A*2602 | x[VTILF]xxxxxx[YF(ML)] | SYFPEITHI |
| A*2603 | x[VFILT]xxxxxx[YFML] | Marsh2000 |
| A*2603 | x[VTILF]xxxxxx[YFML] | SYFPEITHI |
| A*2902 | x[E(M)]xxxxxx[Y(L)] | Marsh2000 |
| A*2902 | x[E(M)]xxxxxx[Y(L)] | SYFPEITHI |
| A*3001 | x[YF(VLMIT)]xxxxxx[L(YFM)] | SYFPEITHI |
| A*3002 | x[YFLV]xxxxxx[Y] | SYFPEITHI |
| A*3003 | x[FYIVL]xxxxxx[Y] | SYFPEITHI |
| A*3004 | xxxxxxxx[YML] | SYFPEITHI |
| A*3101 | xxxxxxxx[R] | Marsh2000 |
| A*3101 | xxxxxxxx[R] | SYFPEITHI |
| A*3201 | x[I]xxxxxxx[W] | Yusim2004 |
| A*3303 | xxxxxxxx[R] | Marsh2000 |
| A*3303 | xxxxxxxx[R] | SYFPEITHI |
| A*6601 | x[TV(APLIC)]xxxxxx[RK] | SYFPEITHI |
| A*6801 | x[VT]xxxxxx[RK] | Marsh2000 |
| A*6801 | x[VT]xxxxxx[RK] | SYFPEITHI |
| A*6802 | x[TV]xxxxxx[VL] | Yusim2004 |
| A*6901 | x[VT(A)]xxxxxx[VL] | Marsh2000 |
| A*6901 | x[VTA]xxxxxx[VL(MQ)] | SYFPEITHI |
| B*07 | x[P]xxxxxx[LF] | SYFPEITHI |
| B*0702 | x[P]xxxxxx[L(F)] | Marsh2000 |
| B*0702 | x[P(V)]xxxxxx[L] | SYFPEITHI |
| B*0703 | x[P]xxxxxxx | Marsh2000 |
| B*0703 | x[P(ND)]xxxxxx[L] | SYFPEITHI |
| B*0705 | x[P]xxxxxxx | Marsh2000 |
| B*0705 | x[P]xxxxxx[L(F)] | SYFPEITHI |
| B*08 | xx[K(R)]x[KR]xxx[L(FM)] | SYFPEITHI |
| B*0801 | xx[K(R)]x[K(RH)]xxxx | Marsh2000 |
| B*0801 | xx[K(R)]xxxxxx | SYFPEITHI |
| B*0802 | xx[K(RY)]x[K(H)]xxxx | Marsh2000 |
| B*0802 | xx[K(RY)]x[K(H)]xxxx | SYFPEITHI |
| B*14 | x[RK]xx[RH]xxx[L] | SYFPEITHI |
| B*1402 | x[R(K)]xx[R(H)]xxx[L] | Marsh2000 |
| B*1501 | x[Q(LMVP)]xxxxxxx[YF] | Marsh2000 |
| B*1501 | x[QL(MVP)]xxxxxxx[FY] | SYFPEITHI |
| B*1502 | xxxxxxxx[YF(M)] | Marsh2000 |
| B*1502 | x[QLVP]xxxxxx[FYM] | SYFPEITHI |
| B*1503 | x[QK]xxxxxx[YF] | SYFPEITHI |
| B*1508 | x[P(A)]xxxxxx[YF] | Marsh2000 |
| B*1508 | x[PA]xxxxxx[YF] | SYFPEITHI |
| B*1509 | x[H]xxxxxx[L(F)] | Marsh2000 |
| B*1509 | x[H]xxxxxx[LFM] | SYFPEITHI |
| B*1510 | x[H]xxxxxx[L(F)] | SYFPEITHI |
| B*1512 | x[Q(LM)]xxxxxx[YF] | SYFPEITHI |
| B*1513 | xxxxxxxx[W] | Marsh2000 |
| B*1513 | x[LIQVPM]xxxxxx[W] | SYFPEITHI |
| B*1516 | x[T(S)]xxxxxx[Y(IVFM)] | Marsh2000 |
| B*1516 | x[ST(F)]xxxxxx[IVYF] | SYFPEITHI |
| B*1517 | x[TS]xxxx[L]x[Y(F)] | Marsh2000 |
| B*1517 | x[TS]xxxxxx[YFLI] | SYFPEITHI |
| B*1518 | x[H]xxxxxx[Y(F)] | SYFPEITHI |
| B*18 | x[E]xxxxxxx | Marsh2000 |
| B*27 | x[R]xxxxxxx | SYFPEITHI |
| B*2701 | x[RQ]xxxxxx[Y] | Marsh2000 |
| B*2701 | x[RQ]xxxxxx[Y] | SYFPEITHI |
| B*2702 | x[R]xxxxxx[FY(ILW)] | Marsh2000 |
| B*2702 | x[R]xxxxxx[FYILW] | SYFPEITHI |
| B*2703 | x[R(M)]xxxxxxx | Marsh2000 |

TABLE 7-continued

HLA Binding Motifs

| Genotype | Motif | Reference |
|---|---|---|
| B*2703 | x[R]xxxxxx[YF(RMWL)] | SYFPEITHI |
| B*2704 | x[R]xxxxxx[YLF] | Marsh2000 |
| B*2704 | x[R]xxxxxx[YLF] | SYFPEITHI |
| B*2705 | x[R(K)]xxxxxxx | Marsh2000 |
| B*2705 | x[R]xxxxxx[LFYRHK(MI)] | SYFPEITHI |
| B*2706 | x[R]xxxxxx[L] | Marsh2000 |
| B*2706 | x[R]xxxxxx[L] | SYFPEITHI |
| B*2707 | x[R]xxxxxx[L] | Marsh2000 |
| B*2707 | x[R]xxxxxx[LF] | SYFPEITHI |
| B*2709 | x[R]xxxxxx[LVFIM] | Marsh2000 |
| B*2710 | x[R]xxxxxx[YF] | Marsh2000 |
| B*35 | x[P(AVYRD)]xxxxxx[YFMLI] | SYFPEITHI |
| B*3501 | x[P(AV)]xxxxxxx | Marsh2000 |
| B*3501 | x[P(AVYRD)]xxxxxx[YFMLI] | SYFPEITHI |
| B*3503 | x[P(A)]xxxxxx[ML(F)] | Marsh2000 |
| B*3503 | x[P(MILFV)]xxxxxx[ML(F)] | SYFPEITHI |
| B*3505 | x[P]xxxxxx[F] | Kenneally2000 |
| B*3701 | x[D(E)]xxxxx[FML][IL] | Marsh2000 |
| B*3701 | x[DE(HPGSL)]xxxxx[FML(QKYL)][IL(TENDQGH)] | SYFPEITHI |
| B*3801 | xxxxxxxx[FL] | Marsh2000 |
| B*3801 | xxxxxxxx[FL(I)] | SYFPEITHI |
| B*3901 | x[RH]xxxxxx[L] | Marsh2000 |
| B*3901 | x[RH]xxxxxx[L(VIM)] | SYFPEITHI |
| B*3902 | x[KQ]xxxxxx[L] | Marsh2000 |
| B*3902 | x[KQ]xxxxxx[L(FM)] | SYFPEITHI |
| B*3909 | x[RH(P)]xxxxxx[LF] | SYFPEITHI |
| B*40 | x[E]xxxxxx[LWMATR] | SYFPEITHI |
| B*4001 | x[E]xxxxxx[L] | Marsh2000 |
| B*4001 | x[E]xxxxxx[L] | SYFPEITHI |
| B*4002 | x[E]xxxxxx[IAVL] | Yusim2004 |
| B*4006 | x[E]xxxxxx[V] | Marsh2000 |
| B*4006 | x[E(P)]xxxxxx[V(AP)] | SYFPEITHI |
| B*4201 | x[P]xxxxxx[L] | Yusim2004 |
| B*44 | x[E]xxxxxx[Y] | SYFPEITHI |
| B*4402 | x[E]xxxxxx[YF] | Marsh2000 |
| B*4402 | x[E(MILD)]xxxxxx[FY] | SYFPEITHI |
| B*4403 | x[E]xxxxxx[YF] | Marsh2000 |
| B*4403 | x[E(MILVD)]xxxxxx[YF] | SYFPEITHI |
| B*4601 | xxxxxxxx[YF] | Marsh2000 |
| B*4601 | x[M(I)]xxxxxx[YF] | SYFPEITHI |
| B*4801 | x[QK]xxxxxx[L] | Marsh2000 |
| B*4801 | x[QK(M)]xxxxxx[L] | SYFPEITHI |
| B*5101 | xxxxxxxx[FI] | Marsh2000 |
| B*5101 | x[APG(WF)]xxxxxx[VI(WMVL)] | SYFPEITHI |
| B*5102 | x[APG]xxxxxx[IV] | Marsh2000 |
| B*5102 | x[APG]xxxxxx[IV] | SYFPEITHI |
| B*5103 | xxxxxxxx[VIF] | Marsh2000 |
| B*5103 | x[APG(FW)]xxxxxx[VIF] | SYFPEITHI |
| B*5201 | xxxxxxx[IV][IV] | Marsh2000 |
| B*5201 | xxxxxxx[IV(MF)][IV(MF)] | SYFPEITHI |
| B*5301 | x[P]xxxxxxx | Marsh2000 |
| B*5301 | x[P]xxxxxx[WFL] | SYFPEITHI |
| B*5401 | x[P]xxxxxxx | Marsh2000 |
| B*5401 | x[P]xxxxxxx | SYFPEITHI |
| B*5501 | x[P]xxxxxxx | Marsh2000 |
| B*5501 | x[P]xxxxxxx | SYFPEITHI |
| B*5502 | x[P]xxxxxxx | Marsh2000 |
| B*5502 | x[P]xxxxxxx | SYFPEITHI |
| B*5601 | x[P]xxxxxxx | Marsh2000 |
| B*5601 | x[P]xxxxxx[A(L)] | SYFPEITHI |
| B*5701 | x[ATS]xxxxxx[FW] | Marsh2000 |
| B*5701 | x[ATS]xxxxxx[FWY] | SYFPEITHI |
| B*5702 | x[ATS]xxxxxx[FW] | Marsh2000 |
| B*5702 | x[ATS]xxxxxx[FW] | SYFPEITHI |
| B*5801 | x[ATS]xxxxxx[WF] | Marsh2000 |
| B*5801 | x[AST(G)]xxxxxx[FW(Y)] | SYFPEITHI |
| B*5802 | x[ST]xxx[R]xx[F] | Marsh2000 |
| B*5802 | x[ST]xxx[R]xx[F] | SYFPEITHI |
| B*6701 | x[P]xxxxxxx | Marsh2000 |
| B*6701 | x[P]xxxxxxx | SYFPEITHI |
| B*7301 | x[R]xxxxxx[P] | Marsh2000 |
| B*7301 | x[R]xxxxxx[P] | SYFPEITHI |
| B*7801 | x[PAG]xxxxxxx | Marsh2000 |
| B*7801 | x[PAG]xxxxx[A(KS)]x | SYFPEITHI |
| B*8101 | x[P]xxxxxx[L] | Yusim2004 |
| Cw*0102 | xx[P]xxxxx[L] | Marsh2000 |

TABLE 7-continued

HLA Binding Motifs

| Genotype | Motif | Reference |
|---|---|---|
| Cw*0102 | x[AL]xxxxxx[L] | SYFPEITHI |
| Cw*0103 | x[AL]xxxxxx[L] | Yusim2004 |
| Cw*0202 | x[A]xxxxxx[L] | Yusim2004 |
| Cw*0203 | x[A]xxxxxx[L] | Yusim2004 |
| Cw*0301 | xxxxxxxx[LFMI] | SYFPEITHI |
| Cw*0302 | x[A]xxxxxx[FWY] | Yusim2004 |
| Cw*0303 | x[A]xxxxxx[LM] | Yusim2004 |
| Cw*0304 | x[A]xxxxxx[LM] | Marsh2000 |
| Cw*0304 | x[A]xxxxxx[LM] | SYFPEITHI |
| Cw*0305 | x[A]xxxxxx[LM] | Yusim2004 |
| Cw*0306 | x[A]xxxxxx[LM] | Yusim2004 |
| Cw*0307 | x[A]xxxxxx[LF] | Yusim2004 |
| Cw*0308 | x[A]xxxxxx[LM] | Yusim2004 |
| Cw*0309 | x[A]xxxxxx[LM] | Yusim2004 |
| Cw*0401 | x[YP]xxxxxxx | Marsh2000 |
| Cw*0401 | x[YPF]xxxxxx[LFM] | SYFPEITHI |
| Cw*0402 | x[YP]xxxxxx[LF] | Yusim2004 |
| Cw*0403 | x[P]xxxxxx[LF] | Yusim2004 |
| Cw*0404 | x[YP]xxxxxx[LF] | Yusim2004 |
| Cw*0405 | x[YP]xxxxxx[LF] | Yusim2004 |
| Cw*0406 | x[P]xxxxxx[LF] | Yusim2004 |
| Cw*0501 | x[A]xxxxxx[LF] | Yusim2004 |
| Cw*0502 | x[A]xxxxxx[LF] | Yusim2004 |
| Cw*0601 | xxxxxxxx[LIVY] | SYFPEITHI |
| Cw*0602 | xxxxxxxx[L] | Marsh2000 |
| Cw*0602 | xxxxxxxx[LIVY] | SYFPEITHI |
| Cw*0603 | x[ALP]xxxxxx[L] | Yusim2004 |
| Cw*0604 | x[RQ]xxxxxx[L] | Yusim2004 |
| Cw*0701 | x[RHK]xxxxxx[Y] | Yusim2004 |
| Cw*0702 | xxxxxxxx[YFL] | SYFPEITHI |
| Cw*0703 | x[YP]xxxxxx[YL] | Yusim2004 |
| Cw*0704 | x[RQ]xxxxxx[LM] | Yusim2004 |
| Cw*0705 | x[RQ]xxxxxx[Y] | Yusim2004 |
| Cw*0706 | x[RHK]xxxxxx[Y] | Yusim2004 |
| Cw*0707 | x[RHK]xxxxxx[YL] | Yusim2004 |
| Cw*0708 | x[RQ]xxxxxx[YL] | Yusim2004 |
| Cw*0709 | x[RHK]xxxxxx[YL] | Yusim2004 |
| Cw*0710 | x[YP]xxxxxx[FWY] | Yusim2004 |
| Cw*0711 | x[R]xxxxxx[LM] | Yusim2004 |
| Cw*0712 | x[R]xxxxxx[LM] | Yusim2004 |
| Cw*0801 | x[A]xxxxxx[LM] | Yusim2004 |
| Cw*0802 | x[A]xxxxxx[LM] | Yusim2004 |
| Cw*0803 | x[A]xxxxxx[LM] | Yusim2004 |
| Cw*0804 | x[A]xxxxxx[LM] | Yusim2004 |
| Cw*0805 | x[A]xxxxxx[LM] | Yusim2004 |
| Cw*0806 | x[A]xxxxxx[LM] | Yusim2004 |
| Cw*1202 | x[A]xxxxxx[FWY] | Yusim2004 |
| Cw*1203 | x[A]xxxxxx[FWY] | Yusim2004 |
| Cw*1204 | x[A]xxxxxx[L] | Yusim2004 |
| Cw*1205 | x[A]xxxxxx[L] | Yusim2004 |
| Cw*1206 | x[A]xxxxxx[FWY] | Yusim2004 |
| Cw*1402 | x[YP]xxxxxx[FWY] | Yusim2004 |
| Cw*1403 | x[YP]xxxxxx[FWY] | Yusim2004 |
| Cw*1404 | x[YP]xxxxxx[FWY] | Yusim2004 |
| Cw*1502 | x[A]xxxxxx[LMYF] | Yusim2004 |
| Cw*1503 | x[A]xxxxxx[LMYF] | Yusim2004 |
| Cw*1504 | x[A]xxxxxx[L] | Yusim2004 |
| Cw*1505 | x[A]xxxxxx[L] | Yusim2004 |
| Cw*1506 | x[A]xxxxxx[LM] | Yusim2004 |
| Cw*1507 | x[A]xxxxxx[LMY] | Yusim2004 |
| Cw*1601 | x[A]xxxxxx[FWY] | Yusim2004 |
| Cw*1602 | x[A]xxxxxx[L] | Yusim2004 |
| Cw*1604 | x[A]xxxxxx[L] | Yusim2004 |
| Cw*1701 | x[A]xxxxxx[L] | Yusim2004 |
| Cw*1702 | x[A]xxxxxx[L] | Yusim2004 |
| Cw*1801 | x[RQ]xxxxxx[LY] | Yusim2004 |
| Cw*1802 | x[RQ]xxxxxx[LY] | Yusim2004 |

The invention claimed is:

1. A complex comprising an MHCI having a peptide derivative bound within its antigen-binding groove, wherein the peptide derivative is selected from the group consisting of:
   (a) a peptide derivative having the general formula A-$X_{aa}$-GIGILTV (SEQ ID NO:3), wherein $X_{aa}$ is a non-natural amino acid that provides increased conformational constraint in the peptide derivative compared to the conformational constraint present in the parent peptide having amino acid sequence AAGIGILTV (SEQ ID NO:1), wherein $X_{aa}$ is selected from the group consisting of [c3a], [c5g], [chg], [cpg], [dfb], [dhl], [phg], and [sta];
   (b) a peptide derivative having the general formula E-Xaa-AGIGILTV (SEQ ID NO:12), wherein Xaa is a non-natural amino acid that provides increased conformational constraint in the peptide derivative compared to the conformational constraint present in the parent peptide having amino acid sequence EAAGIGILTV (SEQ ID NO:2), wherein Xaa is selected from the group consisting of [c3a], [c5g], [chg], [cpg], [dfb], [dhl], [phg], and [sta];
   (c) a peptide derivative having the general formula I-$X_{aa}$-TFKNWPF (SEQ ID NO:22), wherein $X_{aa}$ is a non-natural amino acid that provides increased conformational constraint in the peptide derivative compared to the conformational constraint present in the parent peptide having amino acid sequence ISTFKNWPF (SEQ ID NO:21), wherein $X_{aa}$ is selected from the group consisting of [c3a], [c5g], [chg], [cpg], [dfb], [dhl], [phg], and [sta]; and
   (d) a peptide derivative having the general formula K-$X_{aa}$-RRAIEQL (SEQ ID NO:32), wherein $X_{aa}$ is a non-natural amino acid that provides increased conformational constraint in the peptide derivative compared to the conformational constraint present in the parent peptide having amino acid sequence KVRRAIEQL (SEQ ID NO:31), wherein $X_{aa}$ is selected from the group consisting of [c3a], [c5g], [chg], [cpg], [dfb], [dhl], [phg], and [sta].

2. The complex of claim 1, wherein the peptide derivative is peptide derivative (a).

3. The complex of claim 2, wherein the peptide derivative is A-[cpg]-GIGILTV (SEQ ID NO:7).

4. The complex of claim 1, wherein the peptide derivative is peptide derivative (b).

5. The complex of claim 4, wherein the peptide derivative is selected from the group consisting of E-[chg]-AGIGILTV (SEQ ID NO:15); E-[cpg]-AGIGILTV (SEQ ID NO:16); and E-[dhl]-AGIGILTV (SEQ ID NO:18).

6. The complex of claim 1, wherein the peptide derivative is peptide derivative (c).

7. The complex of claim 6, wherein the peptide derivative is I-[cpg]-TFKNWPF (SEQ ID NO:26).

8. The complex of claim 1, wherein the peptide derivative is peptide derivative (d).

9. The complex of claim 8, wherein the peptide derivative is K-[cpg]-RRAIEQL (SEQ ID NO:36).

* * * * *